(12) United States Patent
Chekalyuk

(10) Patent No.: US 9,618,449 B2
(45) Date of Patent: Apr. 11, 2017

(54) OPTICAL ANALYSIS OF EMISSIONS FROM STIMULATED LIQUIDS

(71) Applicant: The Trustees of Columbia University in the City of New York, New York, NY (US)

(72) Inventor: Alexander Chekalyuk, Bridgewater, NJ (US)

(73) Assignee: The Trustees of Columbia University in the City of New York, New York, NY (US)

(*) Notice: Subject to any disclaimer, the term of this patent is extended or adjusted under 35 U.S.C. 154(b) by 120 days.

(21) Appl. No.: 14/376,297

(22) PCT Filed: Feb. 1, 2013

(86) PCT No.: PCT/US2013/024484
§ 371 (c)(1),
(2) Date: Aug. 1, 2014

(87) PCT Pub. No.: WO2013/116760
PCT Pub. Date: Aug. 8, 2013

(65) Prior Publication Data
US 2015/0000384 A1 Jan. 1, 2015

Related U.S. Application Data

(60) Provisional application No. 61/594,778, filed on Feb. 3, 2012, provisional application No. 61/677,318, filed on Jul. 30, 2012.

(51) Int. Cl.
*G01N 21/00* (2006.01)
*G01N 21/64* (2006.01)
(Continued)

(52) U.S. Cl.
CPC .......... *G01N 21/6402* (2013.01); *G01J 3/021* (2013.01); *G01J 3/0208* (2013.01);
(Continued)

(58) Field of Classification Search
CPC .. G02B 26/0833; G02B 26/08; G02B 26/085; G02B 26/0875; G02B 26/10;
(Continued)

(56) References Cited

U.S. PATENT DOCUMENTS

| | | |
|---|---|---|
| 4,084,905 A | 4/1978 | Schreiber et al. |
| 4,144,452 A | 3/1979 | Harte |

(Continued)

FOREIGN PATENT DOCUMENTS

| | | |
|---|---|---|
| WO | WO-2011069067 A1 | 6/2011 |
| WO | WO-2013116760 A1 | 8/2013 |

OTHER PUBLICATIONS

"International Application Serial No. PCT/US2013/024484, International Search Report mailed Apr. 22, 2013", 3 pgs.
(Continued)

*Primary Examiner* — Michael P Stafira
(74) *Attorney, Agent, or Firm* — Schwegman, Lundberg & Woessner, P.A.

(57) ABSTRACT

Modular systems can be used for optical analysis, including in-situ analysis, of stimulated liquids. An excitation module can include a radiation sources, e.g., a laser, LED, lamp, etc. A detection module can include one or more detectors configured to receive spectral and/or temporal information from a stimulated liquid. Such systems can be used to identify or measure optical emissions including fluorescence or scattering. The efficient excitation of liquid samples and collection of emissions from the samples provides substantial, up to four-fold increase in the emission signal over prior systems. In an example, emission measurements can be (Continued)

conducted in an isolated sample compartment, such as using interchangeable modules for discrete sampling, flow-through sampling, or sampling via fiber probe. The systems and methods described herein can be used to characterize natural aquatic environments, including assessments of phytoplankton pigments, biomass, structure, physiology, organic matter, and oil pollution.

20 Claims, 17 Drawing Sheets

(51) Int. Cl.
*G01J 3/44* (2006.01)
*G01N 33/18* (2006.01)
*G01N 21/65* (2006.01)
*G01J 3/02* (2006.01)
*G01N 33/24* (2006.01)
*G01N 21/05* (2006.01)
*G01N 21/63* (2006.01)

(52) U.S. Cl.
CPC ........... *G01J 3/0216* (2013.01); *G01J 3/0227* (2013.01); *G01J 3/44* (2013.01); *G01J 3/4406* (2013.01); *G01N 21/6408* (2013.01); *G01N 21/6486* (2013.01); *G01N 21/65* (2013.01); *G01N 33/18* (2013.01); *G01N 33/24* (2013.01); *G01J 3/0283* (2013.01); *G01N 21/05* (2013.01); *G01N 2021/634* (2013.01); *G01N 2021/6419* (2013.01); *G01N 2021/6421* (2013.01); *G01N 2021/6463* (2013.01); *G01N 2021/6484* (2013.01); *G01N 2021/651* (2013.01); *G01N 2201/0633* (2013.01); *G01N 2201/06113* (2013.01)

(58) Field of Classification Search
CPC .............. G02B 26/101; G02B 27/0093; G02B 27/2214; G02B 27/225; G02B 21/0008; G02B 2207/101; G02B 2207/109; G02B 26/105; G02B 3/12
See application file for complete search history.

(56) References Cited

U.S. PATENT DOCUMENTS

| | | | |
|---|---|---|---|
| 6,466,316 B2 | 10/2002 | Modlin et al. | |
| 6,794,659 B2 | 9/2004 | Barbieri et al. | |
| 7,209,223 B1 | 4/2007 | Hull et al. | |
| 7,251,026 B2 | 7/2007 | Gilby | |
| 7,295,316 B2 | 11/2007 | Boege et al. | |
| 7,595,881 B2 | 9/2009 | Leonard et al. | |
| 8,970,841 B2 * | 3/2015 | Chekalyuk | G01J 3/02 356/317 |
| 2007/0237679 A1 * | 10/2007 | Hegazi | G01N 21/6402 422/82.08 |
| 2008/0297808 A1 * | 12/2008 | Riza | G01B 9/02004 356/503 |

OTHER PUBLICATIONS

"International Application Serial No. PCT/US2013/024484, Preliminary Amendment filed Aug. 5, 2014", 7 pgs.

"International Application Serial No. PCT/US2013/024484, Written Opinion mailed Apr. 22, 2013", 6 pgs.

Chekalyuk, Alexander, et al., "Advanced laser fluorometry of natural aquatic environments", Limnology and Oceanography: Methods, vol. 6, (2008), 591-609.

Chekalyuk, Alexander M, et al., "Laser fluorescence analysis of phytoplankton across a frontal zone in the California Current ecosystem", Journal of Plankton Research, 2012, [online]. Retrieved from the Internet: <http://plankt.oxfordjournals.org/content/early/2012/05/16/plankt.fbs034.full.pdf>, (2012), 1-17.

Chekalyuk, Alexander, et al., "Photo-physiological variability in phytoplankton chlorophyll fluorescence and assessment of chlorophyll concentration", Optics Express, vol. 19, No. 23, (Nov. 7, 2011), 22643-22658.

Tan, Han Yen, et al., "Filterless fluorometry with enhanced sensitivity", Journal of Fluorescence, 19(2), (Mar. 2009), 375-379.

International Application Serial No. PCT/US2013/024484, International Preliminary Report on Patentability mailed Aug. 14, 2014, 8 pgs.

* cited by examiner

OPTICAL ANALYSIS OF EMISSIONS FROM STIMULATED LIQUIDS

CLAIM OF PRIORITY

This application is a U.S. National Stage Filing under 35 U.S.C. 371 from International Application No. PCT/US2013/024484, filed on 1 Feb. 2013, and published as WO 2013/116760 A1 on 8 Aug. 2013, which claims the benefit of priority of United States Provisional Patent Application Ser. No. 61/594,778, filed Feb. 3, 2012, entitled OPTIMIZED OPTICAL SETUP FOR STIMULATION, COLLECTION AND SPECTRAL FILTRATION OF OPTICAL EMISSION IN LIQUIDS, and United States Provisional Patent Application Ser. No. 61/677,318, filed Jul. 30, 2012, entitled AN OPTICAL SETUP FOR SPECTRALLY AND TEMPORALLY RESOLVED MEASUREMENTS OF LASER-STIMULATED EMISSION IN NATURAL WATERS, each of which are incorporated herein by reference in their entirety.

STATEMENT REGARDING FEDERALLY SPONSORED RESEARCH OR DEVELOPMENT

This invention was made with government support under award number N000141010205 awarded by the National Oceanographic Partnership Program, the National Science Foundation, and the Office of Naval Research. The government has certain rights in this invention.

BACKGROUND

Fluorescence analysis of natural aquatic environments, such as including oceanic, estuarine, or fresh waters, can be based on measurements of water emission, such as in response to a laser, LED, Xenon flash tube, or other excitation sources. Fluorescence analysis can be used to retrieve information about the fluorescent constituents in a water body or sample. For example, in vivo fluorescence of chlorophyll-a (Chl-a) and accessory phycobiliprotein (PBP) pigments can be broadly used as an index of phytoplankton biomass, and can provide useful information for structural or photo-physiological characterization of mixed algal populations. A broadband chromophoric dissolved organic matter (CDOM) fluorescence emission can be used to assess CDOM abundance, or to assess qualitative characteristics of CDOM.

There can be significant spectral complexity of the actively stimulated emission of natural waters. This can be due to an overlap between water Raman (WR) scattering and the fluorescence bands of aquatic constituents. Most commercially available field fluorometers use spectrally broad excitation sources and relatively narrow discrete band emission detection, and often do not provide adequate spectral resolution to ensure reliable assessment of constituents in spectrally complex natural waters.

Spectral and temporal measurements of water emission can be performed using a various optical configurations. Some examples use a plurality of excitation sources that produce different excitation signals with different wavelengths. Hull et al., in U.S. Pat. No. 7,209,223, entitled OPTICAL DEVICE FOR MEASURING OPTICAL PROPERTIES OF A SAMPLE AND METHOD RELATING THERETO, refers to a device with a plurality of excitation sources positioned on a housing incident to a sample in a flow-through measurement cell, and detecting a continuous, broadband spectrum of emission wavelengths. Gilby, in U.S. Pat. No. 7,251,026, entitled FLUORESCENCE DETECTOR GEOMETRY, describes a photometric flow cell that uses a retro-reflecting mirror to increase a path-length of an excitation signal. Fluorescence and absorbance characteristics, such as over multiple wavelengths, can be detected. Schrieber et al., in U.S. Pat. No. 4,084,905, entitled APPARATUS FOR DETECTING AND MEASURING FLUORESCENCE EMISSION, refers to detecting and measuring a time course of fluorescence using a "Kautsky" apparatus that includes an excitation source, a filter, and photo-detector.

Overview

Examples of Advanced Laser Fluorescence (ALF) methods and instruments, and spectral deconvolution techniques, are described in Chekalyuk, PCT Patent Publication WO 2011/069067, entitled SPECTRAL AND TEMPORAL LASER FLUORESCENCE ANALYSIS SUCH AS FOR NATURAL AQUATIC ENVIRONMENTS, which is hereby incorporated herein by reference in its entirety. The ALF methods and instruments can be used to characterize aquatic environments by combining high-resolution spectrally and temporally resolved measurements of light-stimulated emissions (LSE). Real-time LSE spectral deconvolution (SDC) can be used to assess key biogeochemical variables, such as including chlorophyll-a (Chl-a), phycobiliprotein (PBP) pigments, and chromophoric dissolved organic matter (CDOM). Several spectral types of phycoerythrin (PE) can be discriminated for detection and characterization of PBP-containing phytoplankton and cyanobacteria. In an example, spectral correction of temporally-resolved pump-during-probe (PDP) measurements of variable fluorescence, Fv/Fm, can yield improved assessments of phytoplankton photosynthetic capacity. In other examples, temporally-resolved Fv/Fm measurements can be used for improved assessment of Chl-a and phytoplankton biomass. A series of field measurements in diverse water types have demonstrated ALF's utility as an informative integrated tool for aquatic research and observations. ALF methods and instruments can be used for oceanographic research, validation of satellite ocean color data, and environmental monitoring, among other applications. In an example, oil and oil products can be detected and identified, such as in natural waters, using fluorescence analysis.

The combined spectrally and temporally resolved analysis can provide accurate and comprehensive characterization of the fluorescence constituents in natural aquatic environments. Instruments capable of the concurrent spectral and temporal emission measurements, such as the Advanced Laser Fluorometer (see, e.g., Chekalyuk, PCT Patent Publication WO 2011/069067), can provide valuable flow-through measurements and discrete sample analysis.

The present inventor has recognized, among other things, that a problem to be solved can include optimizing an optical system to maximize an intensity of light-induced emissions, such as from optically thin liquids, and can further include optimizing instrument design and methodologies to further extend analytical capabilities and applications for optical characterization of liquid properties. In an example, the present subject matter can provide a solution to this problem, such as using an optical configuration that incorporates a back-reflecting mirror that is optically adjacent to an analyzed liquid sample, such as in a measurement cell. The mirror can be configured to direct a stimulation energy through a liquid sample of interest such that the liquid sample is stimulated by the direct stimulation energy and the back-reflected stimulation energy. In an example, multiple emission detectors can be used to receive spectral or temporally-resolved emission information from the liquid sample. In an example, the present subject matter can further include one or more other optical components, in a light path between the back-reflecting mirror and the one or more emission detectors, to further reflect emissions from the liquid sample back through the liquid sample and toward one of the emission detectors, thus providing a substantial increase in the emission signal detected by the system. In an example, such a system can be configured to conduct measurements in various settings, including bench-top and wall-mount configurations, and external configurations, such as including remote measurements using a fiber probe.

The present inventor has recognized, among other things, that a problem to be solved can include providing an optical apparatus that can be used in situ to conduct various spectrally and temporally resolved measurements, such as concurrently, for better characterization of bio-geochemical processes in natural environments at various depths. In an example, the present subject matter can provide a solution to this problem, such as using a fluorometer with discrete optics or a fiber probe. In an example, a dichroic splitter can be used to direct different spectral portions of optical emissions to different types of sensors that can be used to detect different temporal and spectral information about the emissions. In an example, an optical configuration including the dichroic splitter can be used to provide various new instrument configurations for comprehensive characterization of fluorescence constituents in natural aquatic environments, such as by combining spectral and temporal analysis of constituent-specific fluorescence signatures. In an example, an ALF instrument can be configured for in situ high-resolution characterization of spatial patterns of phytoplankton phytoplankton biomass, physiological properties, photosynthetic potency, and community structure complemented with distributions of CDOM, oil pollutants, and other fluorescence constituents. Other fiber-probe, benchtop, or over-the-shoulder instrument configurations for various laboratory and field applications can be also provided using the present optical arrangements.

The present inventor has recognized, among other things, that a problem to be solved can include providing a single optical apparatus that can be easily configured for discrete sample measurements or flow-through sample analysis for optically-optimized measurements in an instrument sample compartment, as well as in external sample analysis. In an example, the present subject matter can provide a solution to this problem, such as by statically arranging optical source and filter components in an enclosure, wherein a portion of the enclosure that includes a measurement module is user-accessible and removable from a front or side panel. In an example, interchangeable sampling modules can include a flow-through cell, a discrete sampling cell (e.g., a reusable or disposable cell), or a fiber probe adaptor, among other sample-holding or input devices.

In an example, optical systems described herein can include one or more emission detectors, such as to detect spectral or temporal emissions from a laser-stimulated liquid volume. In an example, an optical system comprising two emission detectors can include (i) two spectrometers, (ii) two photomultipliers, two photodiodes, or one photomultiplier and one photodiode; or (iii) one spectrometer and one photomultiplier to conduct (a) spectral measurements in different spectral ranges, (b) temporal measurements in different spectral ranges or over different temporal scales; or (c) spectral and temporal measurements, each in its own spectral range.

This overview is intended to provide an overview of subject matter of the present patent application. It is not intended to provide an exclusive or exhaustive explanation of the invention. The detailed description is included to provide further information about the present patent application.

BRIEF DESCRIPTION OF THE DRAWINGS

In the drawings, which are not necessarily drawn to scale, like numerals may describe similar components in different views. Like numerals having different letter suffixes may represent different instances of similar components. The drawings illustrate generally, by way of example, but not by way of limitation, various embodiments discussed in the present document.

DETAILED DESCRIPTION

Examples of Advanced Laser Fluorescence (ALF) methods and instruments, and spectral deconvolution techniques, are described in Chekalyuk, PCT Patent Publication WO 2011/069067, entitled SPECTRAL AND TEMPORAL LASER FLUORESCENCE ANALYSIS SUCH AS FOR NATURAL AQUATIC ENVIRONMENTS, which is hereby incorporated herein by reference in its entirety. The ALF methods and instruments can be used to characterize aquatic environments by combining high-resolution spectrally and temporally resolved measurements of laser-stimulated emissions (LSE). Real-time LSE spectral deconvolution (SDC) can be used to assess key biogeochemical variables, such as including chlorophyll-a (Chl-a), phycobiliprotein (PBP) pigments, and chromophoric dissolved organic matter (CDOM). Several spectral types of phycoerythrin (PE) can be discriminated for detection and characterization of PBP-containing phytoplankton and cyanobacteria. In an example, spectral correction of temporally-resolved pump-during-probe (PDP) measurements of variable fluorescence, Fv/Fm, can yield improved assessments of phytoplankton photosynthetic capacity. In other examples, temporally-resolved Fv/Fm measurements can be used for improved assessment of Chl-a and phytoplankton biomass. A series of flow-through ALF measurements in diverse water types have demonstrated ALF's utility as an informative integrated tool for aquatic research and observations. ALF methods and instruments can be used for oceanographic research, validation of satellite ocean color data, and environmental monitoring, among other tasks.

Various optical configurations can be used to measure stimulated emissions from liquids, including via in situ, remote, and flow-through measurements, and discrete sample analysis. Such optical configurations can be used for measurements of fluorescence, Raman and elastic scattering, and other types of optical emissions. In an example, liquids to be stimulated can include natural waters, solutions, solvents such as ethanol, methanol, or acetone, or other liquids.

Figure 1:
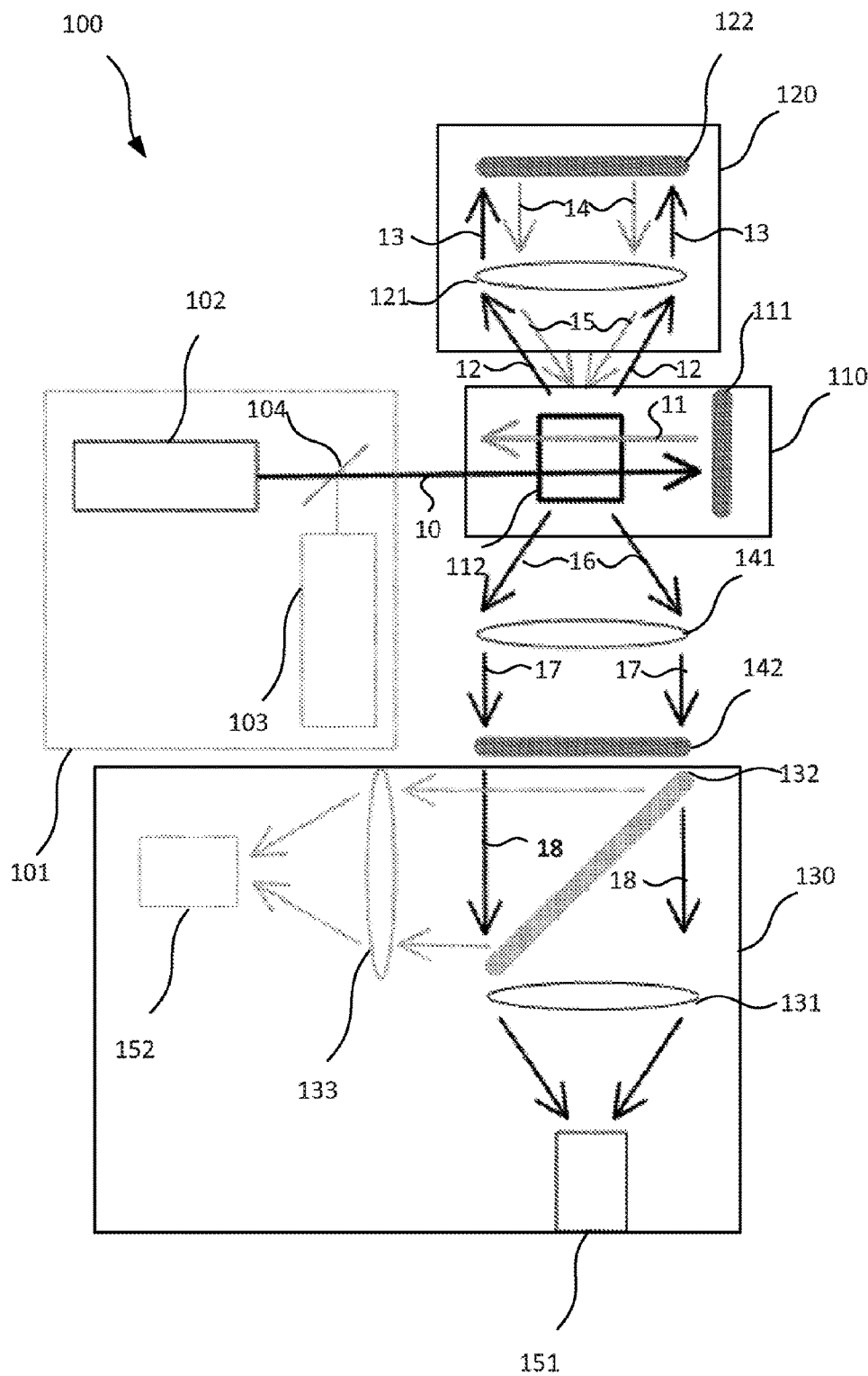
FIG. 1 illustrates generally an example of an optical system.

FIG. 1 illustrates generally an example of a first optical system 100 for stimulation, collection, and single-channel spectral filtration of optical emissions from liquids. The first optical system 100, such as a bench-top optical system, can include an excitation module 101, a sample module 110, an emission enhancement module 120, and a detection module 130, all in optical communication. In an example, any one or more of the modules can be removable, interchangeable, or fixed, such as fixed within an instrument case. In an example, only the sample module 110 is interchangeable, and the other modules are fixed within the instrument case.

The first optical system 100 provides efficient excitation and collection of optical emissions from a liquid volume in the sample module 110, such as using one or more collimated light sources originating in the excitation module 101 as an excitation energy source. The first optical system 100 can include one or more sensors for analysis of optical emissions from liquids in the sample module 110. In an example, the first optical system 100 is configured to provide up to a four-fold overall increase in an emission signals collected from the liquid volume, such as compared to a conventional 90-degree measurement scheme. In an example, an approximately two-fold increase in excitation efficiency over the conventional scheme can be achieved using one or more mirror elements to reflect the excitation energy back into the liquid volume, after an initial excitation by the excitation energy, to stimulate additional emission.

In an example, the excitation module 101 comprises one or more excitation sources, such as configured to provide an electromagnetic energy (e.g., light energy, such as broadband or narrow-band). For example, the first optical system 100 includes a first excitation source 102 and a second excitation source 103. In an example, the excitation sources can include, among other devices, lasers (e.g., configured to provide one or more of an emission at 375 nm, 405 nm, or 514 nm), light-emitting diodes (LEDs), filament lamps, or arc lamps coupled with collimating optics. In an example, one or more of the excitation sources can be configured to provide collimated light. In an example, the excitation module 101 includes a source dichroic mirror 104 configured to receive an excitation energy from one or more of the excitation sources and direct the received excitation energy toward the sample module 110. In an example, the various sources can have various corresponding lens assemblies (not shown in FIG. 1) configured to collimate or focus excitation energy from the sources toward the sample module 110, such as to adjust an intensity of the excitation energy received by the sample module 110. In an example, excitation energy generated by one or more sources in the excitation module 101 can form a coaxial excitation energy directed along a first light path 10 to exit the excitation module 101 and enter the sample module 110.

In an example, the sample module 110 includes a sample cell 112 and a back-reflecting mirror 111. The first light path 10 can extend into the sample module 110, through the sample cell 112 (e.g., comprising an optically-thin liquid), and impinge on the back-reflecting mirror 111. The back-reflecting mirror 111 can be a 100% mirror, such as in a spectral band of an excitation energy provided by one or more sources in the excitation module 101. The back-reflecting mirror 111 can be configured to receive an excitation energy from the excitation module 101, after at least a portion of the excitation energy passes through the sample cell 112. At least a portion of the excitation energy received by the back-reflecting mirror 111 can be redirected back into the sample cell 112, such as to stimulate the same or different portion of the liquid volume. In an example, a liquid sample in the sample cell 112 can respond to the combination of the initial excitation energy provided to the sample cell 112 and the back-reflected portion of the excitation energy with increased emission intensity, such as up to about a two-fold increase in responsive emission intensity. In the example of FIG. 1, the light path 10 represents the initial excitation energy provided to the sample cell 112, and the light path 11 represents the back-reflected portion of the excitation energy.

The first optical system 100, in the example of FIG. 1, includes the optional emission enhancement module 120. The emission enhancement module 120 includes a first lens 121 and a mirror 122. The first lens 121 can be disposed adjacent to the sample module 110 and can be focused toward the sample cell 112 such that emissions from the sample cell 112 enter the first lens 121. In an example, the first lens 121 can be coated for minimum spectral reflection. In an example, the first lens 121 is a collimating lens. For example, a first emission 12 originating from the sample cell 112 can be received at the first lens 121 and collimated into a first collimated emission 13.

In an example, the collimated emission 13 can be directed toward the mirror 122. The mirror 122 can be configured such that it is substantially reflective in the spectral range of a detector 151 (e.g., in the detection module 130). In an example, the collimated emission 13 can be reflected by the mirror 122 (e.g., shown in FIG. 1 as the reflected collimated emission 14) toward the first lens 121, and focused by the first lens 121 to provide a focused emission 15 directed toward the sample module 110. The focused emission 15 can be directed toward the sample cell 112, such as to further stimulate contents of the sample cell 112. In an example, the focused emission 15 can pass through the sample cell 112 (e.g., comprising an optically-thin liquid volume of interest) and exit the sample cell 112, such as along with a second, direct emission from the liquid volume (e.g., in the same direction), as a composite emission 16. In an example, this arrangement can provide a two-fold increase in the optical efficiency of the system, such as compared to a conventional 90-degree scheme.

In an example, the first optical system 100 includes a second lens 141 and a first filter 142. The composite emission 16 can exit the sample cell 112 and the sample module 110 and can be received by the second lens 141. In an example, the second lens 141 is a collimating lens, and can be coated for minimum spectral reflection. The second lens 141 can be configured to pass the composite emission 16 as a collimated composite emission 17. The composite collimated emission can be received by the first filter 142.

In an example, the first filter 142 can be an optical filter that is configured to narrow a spectral range of an optical signal. For example, the composite collimated emission beam 17 can be passed through the first filter 142 to narrow a spectral range of a filtered emission 18 from the first filter 142. In an example, the composite collimated emission 17 can be provided at an optimal angle of incidence relative to the first filter 142, such as at about 90 degrees. In an example, a 45 degree folding mirror (not shown in FIG. 1) can be disposed between the second lens 141 and the first filter 142, such as to provide a more compact optical arrangement of the first optical system 100. For example, a combination of an optical splitter 132, a focusing lens 133, and a second detector 152 can be used with the 45 degree folding mirror to achieve a more compact arrangement.

In an example, the filtered emission 18 can be received using one or more elements in the detection module 130. The detection module 130 can include a first detector 151 and an optional third lens 131. The detection module 130 can optionally further include the second lens 141 and the first filter 142. The third lens 131 can be a focusing lens, such as configured to receive the filtered emission 18 and focus it on a photo-sensitive region of the first detector 151. In an example, an input to the first detector 151 can be provided using an optical fiber (not shown in FIG. 1). For example, the focused filtered emission 18 can be introduced to a first end of an optical fiber, and an opposite end of the optical fiber can be coupled to the input of the first detector 151. In an example, a 45 degree folding mirror (not shown in FIG. 1) can be disposed between the first filter 142 and the third lens 131, such as to provide a more compact optical arrangement of the first optical system 100.

The first optical system 100 can optionally include an optical splitter 132 and a second detector 152. One or more lenses or filters (e.g., focusing lens 133 shown in FIG. 1) can be disposed between the optical splitter 132 and the second detector 152, such as to filter or further focus a portion of the focused filtered emission 18 toward the second detector 152. In an example, the optical splitter 132 can be a dichroic filter configured to spectrally filter a portion of the filtered emission 18. One or more other detectors can be added using additional optical splitters and/or focusing lenses similar to those used for the second detector (D2).

Figure 2:
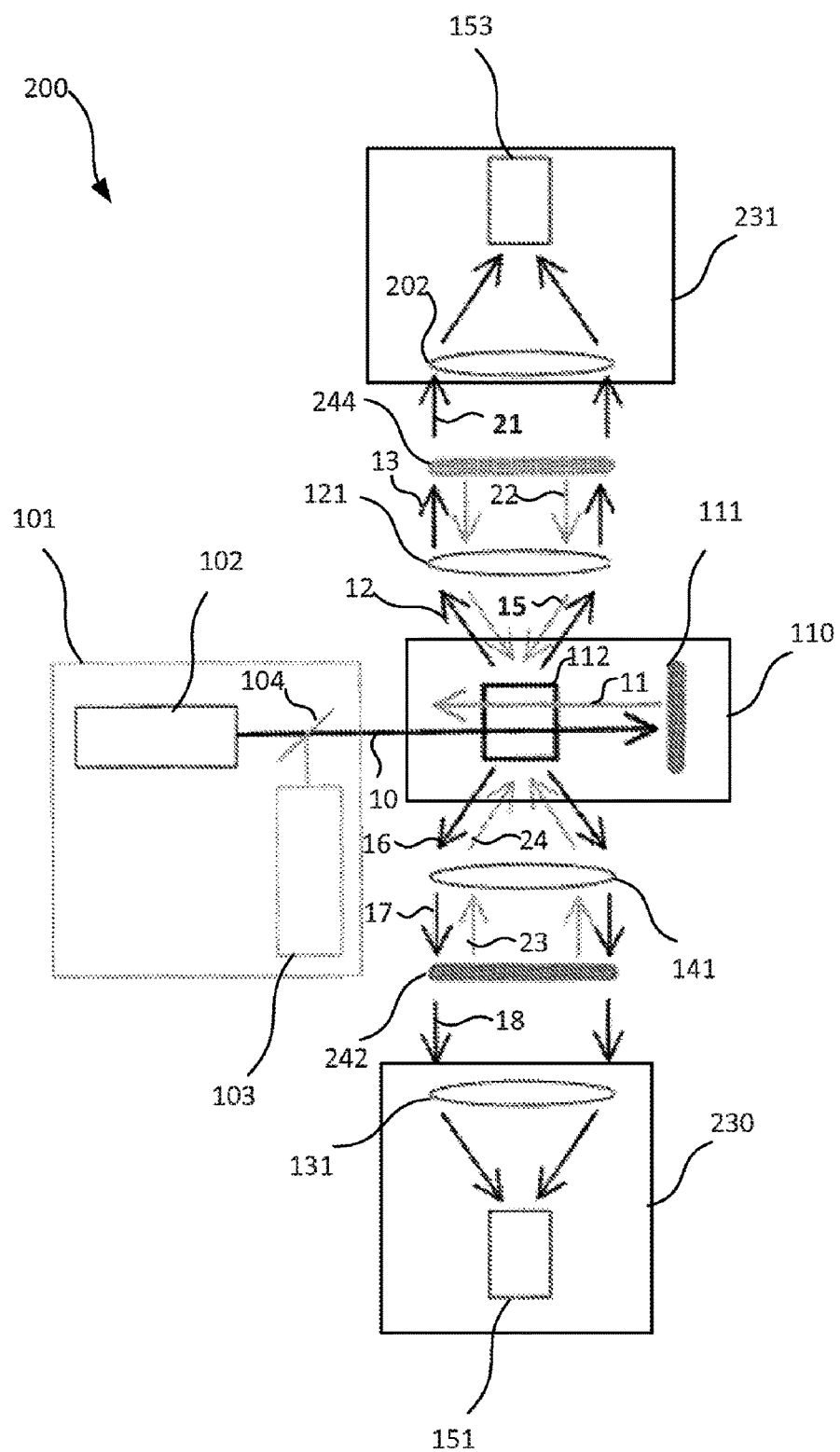
FIG. 2 illustrates generally an example of an optical system configured for dual-channel analysis.

FIG. 2 illustrates generally an example of a second optical system 200 for stimulation, collection, and multi-channel spectral filtration of optical emissions from liquids. The second optical system 200, such as a bench-top optical system, can include the excitation module 101, the sample module 110, a first detection module 230, and a second detection module 231, among other components, such as all in optical communication. In an example, any one or more of the modules and other components can be interchangeable or fixed, such as fixed within an instrument case. In an example, only the sample module 110 is interchangeable, and the other modules are fixed within the instrument case.

In an example, the second optical system 200 includes many of the elements of the first optical system 100. Such common elements are referenced in FIGS. 1 and 2 using common reference numerals. The second optical system 200 can be configured to provide efficient excitation of contents of the sample module 110, such as using one or more collimated emission energy sources (e.g., using the first and second excitation sources 102 and 103). Similarly to the first optical system 100 of FIG. 1, the second optical system 200 achieves increased optical efficiency due in part to reflection of the excitation energy (e.g., the energy provided along the first light path 10) back toward contents of the sample cell 112.

In the example of FIG. 2, the second optical system 200 includes first and second detection modules 230 and 231 having respective first and second emission detectors 151 and 153. In an example, each of the first and second detection modules 230 and 231 is configured to receive a collimated emission using a lens that focuses the received collimated emission on the respective emission detector. For example, the third lens 131 can be configured to receive the filtered emission 18 and pass a focused emission signal on a photo-sensitive region of the first detector 151, such as described above. The fourth lens 202 can be similarly configured to receive a filtered emission 21 and pass a focused emission signal on a photo-sensitive region of the second detector 153.

In an example, the second optical system 200 can be configured to measure emissions from contents of the sample cell 122 in two or more non-overlapping spectral ranges. For example, the first detector 151 can be configured to receive particular spectral or temporal emissions information in a first spectral range not exceeding $\lambda_1$, and the second detector 153 can be configured to receive particular spectral or temporal emissions information in a spectral range that exceeds $\lambda_2$. In an example where $\lambda_1$ is less than $\lambda_2$, there can be no overlap between the spectral ranges of the first and second detectors 151 and 153. In an example, the optical system can be configured for such a scenario, such as using a short-pass interference filter 242 and a long-pass interference filter 244. The short-pass interference filter 242 can have a transparency transition from 100% to 0% at $\lambda_1$. The long-pass interference filter 244 can have a transparency transition from 0% to 100% at $\lambda_2$. In this example, the long-pass interference filter 244 can be configured to pass a first filtered emission 21 to the second detection module 231 (e.g., to a focusing lens 202 in the second detection module 231). That is, the long-pass interference filter 244 can be configured to pass a longer-wavelength emission portion of the first emission 12 to the second detector 153. In an example, the long-pass interference filter 244 can be configured to reflect a short-wavelength emission portion 22 (e.g., corresponding to wavelengths $<\lambda_2$) back toward the first lens 121. After focusing by the first lens 121, this portion of emission can be added to the composite emission 16 emitted from the sample module 110 towards the first detection module 230. In an example, the composite emission 16 can be collimated by the second lens 141 and filtered by the short-pass interference filter 242. Thus, short-wavelength portions (e.g., corresponding to wavelengths $<\lambda_1$) of the composite emission 16 can be passed toward the first detection module 230, and longer-wavelength portions (e.g., corresponding to wavelengths $>\lambda_1$) can be redirected back toward the second lens 141. In this example, the emissive content back-reflected by the long-pass interference filter 244 and short-pass interference filter 242 can provide substantial enhancement of the various spectral portions provided to the respective first and second emission detectors 151 and 153. Application examples can include measurement of Stokes and anti-Stokes components of Raman scattering in liquid samples using such an optical scheme.

Although the second optical system 200 provides for the most substantial efficiency gains when the spectral ranges of emission detection by the first and second emission detectors 151 and 153 do not overlap, the second optical system 200 nonetheless provides efficiency improvements if there is an overlap in the spectral ranges of the interference filters 242 and 244. In the latter example, an improvement in a spectral range of emissions outside of the spectral overlap can be achieved.

Figure 3:
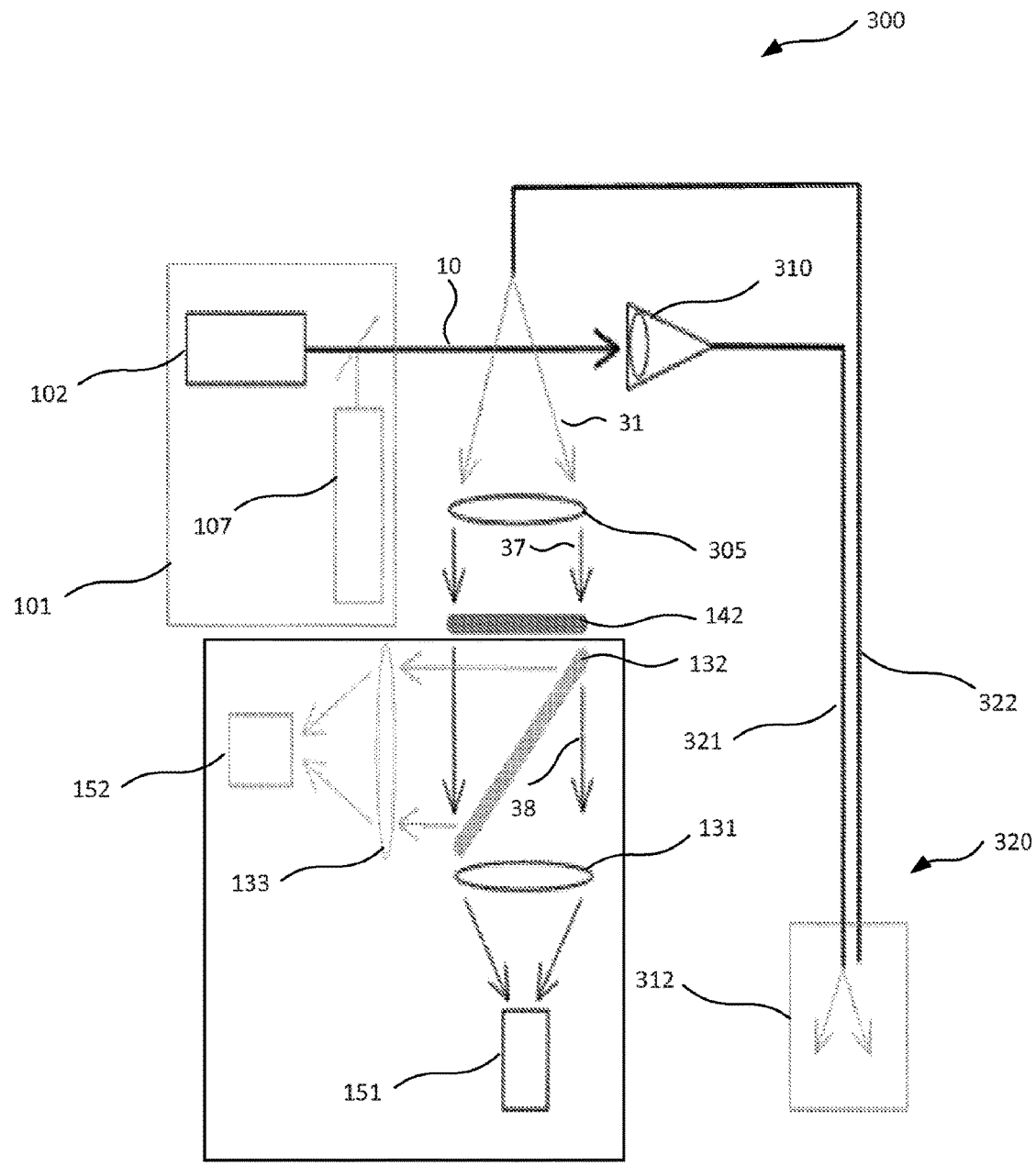
FIG. 3 illustrates generally an example of an optical system that includes a fiber probe.

FIG. 3 illustrates generally an example of a third optical system 300 with a fiber probe 320. The third optical system 300 can include a fiber probe 320 for remote optical stimulation of a liquid volume and measurement of emissions from the liquid volume when the analyzed liquid volume is located outside of an instrument case (e.g., the instrument case including the excitation module 101, the detection module 130, etc.).

In an example, the fiber probe 320 is physically and/or optically coupled to the excitation module 101 and the detection module 130 using a fiber probe adapter 310. The fiber probe 320 can be a multi-fiber-leg assembly, such as comprising an excitation leg 321 and a collection leg 322. In an example, the fiber probe adapter 310 can include an optical element configured to focus an excitation energy (e.g., received from the excitation module 101) into the excitation leg 321. In an example, an end of the excitation leg 321 can be submerged in, or placed adjacent to, a liquid volume of interest 312. The collection leg 322 can be used to receive optical back-scatter emissions 31 from the stimulated liquid volume of interest 312. Optical back-scatter emissions 31 received from the sample can be directed toward a collimating lens 305. A collimated emission signal 37 can be passed from the collimating lens 305 to the first filter 142 and the detection module 130. The filtered collimated emission signal 38 can be further processed in the detection module 130, such as described above in the discussion of FIG. 1. In an example, the first and third optical systems 100 and 300 can be commonly implemented using a modular instrument. For example, in a particular modular example of the first and third optical system 100 and 300, the sample module 110 can be removed from the first optical system (e.g., including removing first lens 121 and mirror 122), and replaced with the fiber probe adapter 310. In this manner, a common excitation module 101 and detection module 130 can function with both the sample module 110 and the fiber probe 320.

Figure 4:
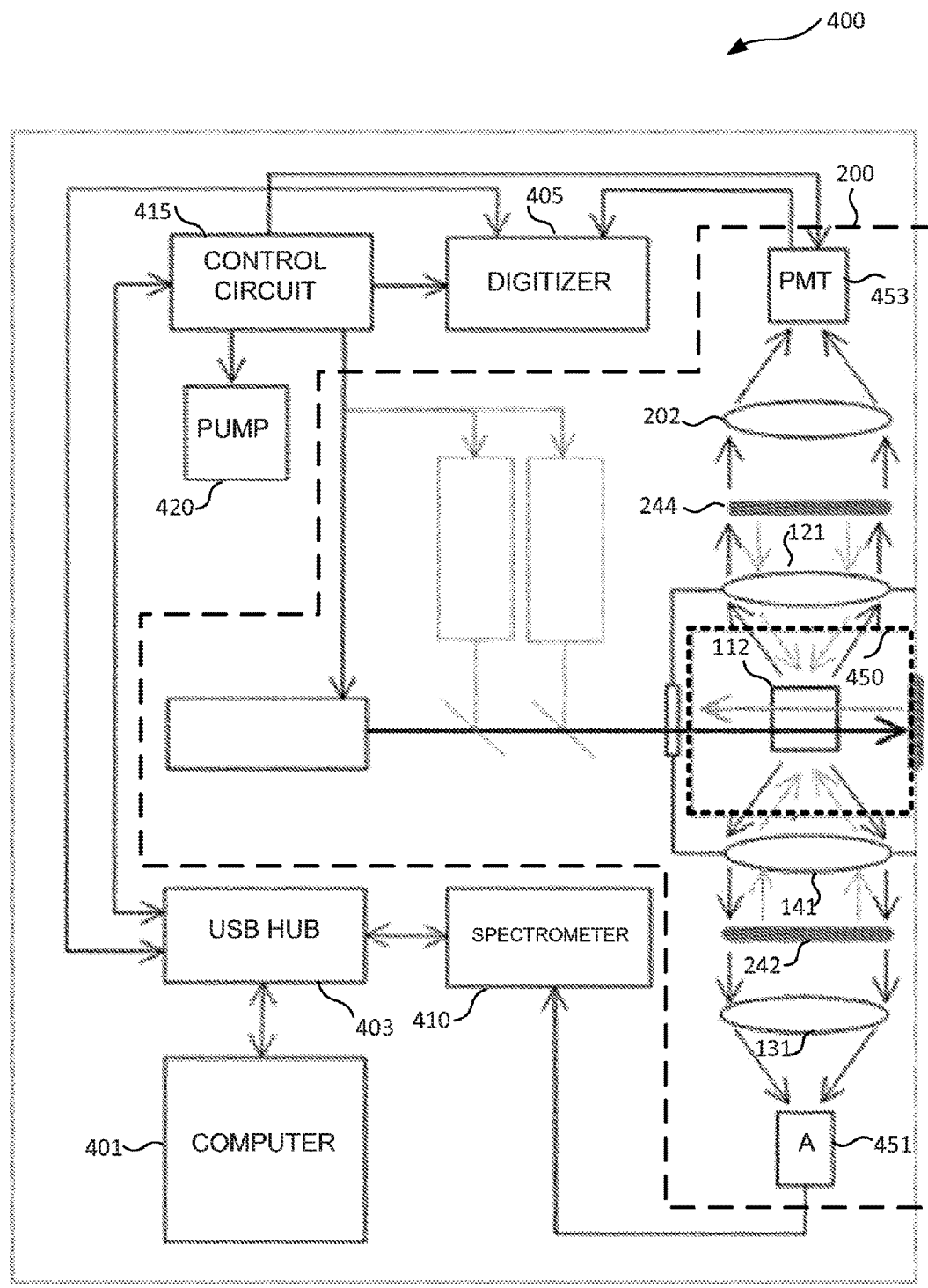
FIG. 4 illustrates generally a block diagram of an example of an optical system.

FIG. 4 illustrates generally a block diagram of an example 400 of an optical system for spectral and temporal analysis of emissions, e.g., from natural waters. The example 400 is configured, generally, using portions of the example of the optical system 200. The example 400 includes, among other components, a broadband spectrometer 410, a photomultiplier (PMT) 453 coupled to a waveform digitizer 405 (e.g., configured to receive information about temporally resolved emissions), a control circuit 415 coupled to a computer 401 via an electronic interface (e.g., USB hub 403). In an example, the control circuit 415 can be coupled to a pump 420, such as for driving flow of a sample volume through the measurement cell 112. The second optical system 200 is incorporated into the example 400. For example, the second detector 153 corresponds to the PMT 453, and the first detector 151 corresponds to the spectrometer 410 (e.g., via the spectrometer fiber coupling 451). In the example 400, the control circuit 415 is coupled to the excitation module 101 portion of the optical system 200. The control circuit 415 can issue control signals to the one or more excitation sources, such as to selectively initiate, cease, or adjust the one or more excitation sources.

To briefly recap the discussion above of the second optical system 200, the optical system 200 incorporated in the example 400 includes two emission collection-filtration optical units. For example, stimulated emissions (e.g., laser stimulated) of the sample cell 112 can be collected and collimated by the second lens 141, filtered by the long-pass filter 242 (or other filter), and focused by the third lens 131 (e.g., a fiber adaptor) in an input end 451 of a fiber coupled to the spectrometer. Similarly, stimulated emissions of the sample cell 112 can be collected and collimated by the first lens 121, filtered by the band-pass interference filter 244 (e.g., transparent for the band of Chl-a fluorescence between about 670 and 700 nm) (or other filter), and focused by the fourth lens 202 toward the PMT 453. In an example, portions of the emissions that are outside of the band-pass interference filter 244 pass band (e.g., a red band having a bandwidth of about 30 nm) can be reflected back toward the sample cell 112 and the spectrometer fiber coupling 451, as described above in the discussion of FIG. 2. Using such a configuration, an attendant enhancement in spectral emission can be observed (see, e.g., FIG. 16).

In an example, an instrument configuration for spectral characterization of fluorescence constituents in natural water samples, such as include phytoplankton pigments and CDOM, and assessment of phytoplankton photochemical efficiency can include the example 400, wherein the excitation module 101 includes a single 514 nm laser. In an example, an instrument configuration for more detailed spectral characterization and assessment, including for CDOM and oil pollutants, in addition to phytoplankton, can include the example 400, wherein the excitation module 101 includes three lasers: a first laser at 375 nm, a second at 405 nm, and a third at 514 nm. The lasers operational at wavelengths of 375 nm and 405 nm can provide additional analytical capabilities.

Figure 15A:
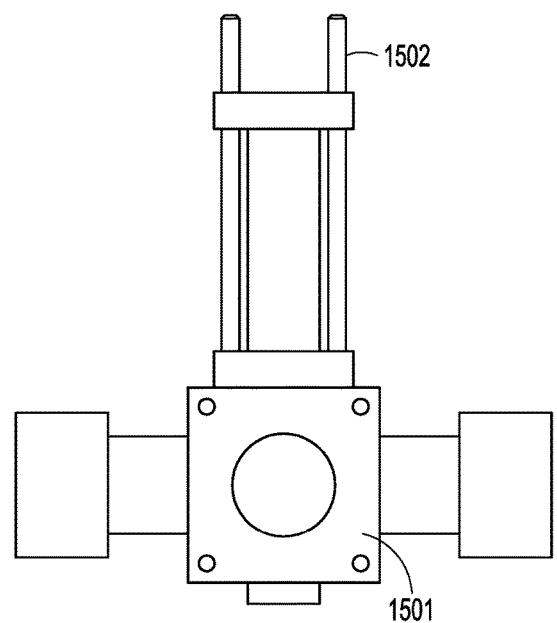
FIG. 15A illustrates generally an example of a user-interchangeable flow cell compartment.
Figure 15B:
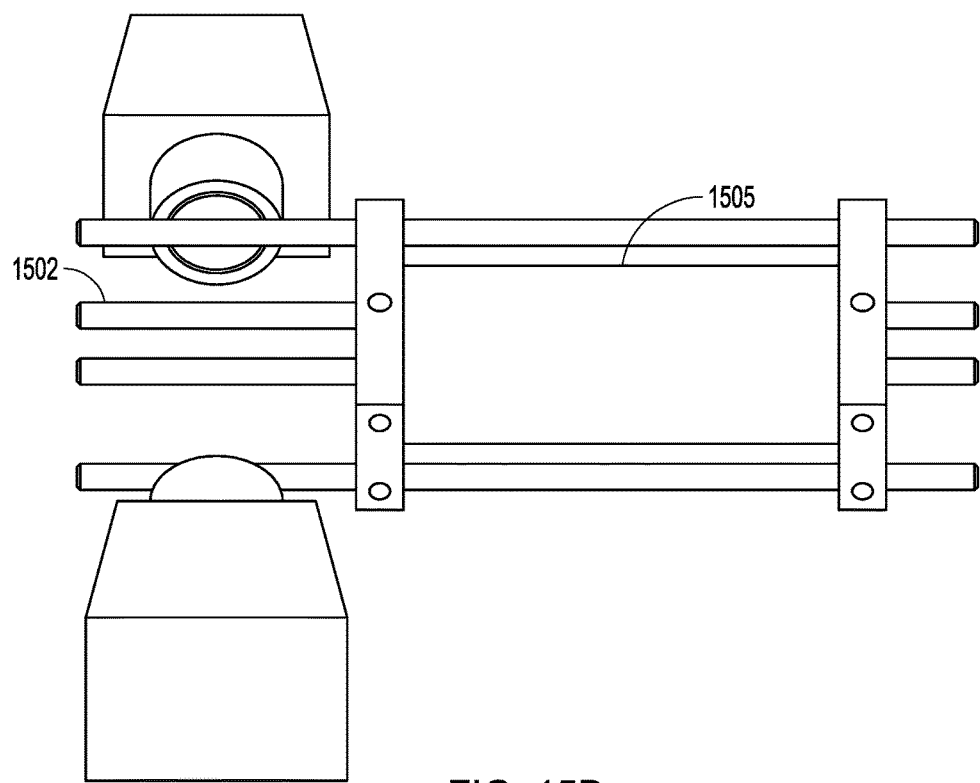
FIG. 15B illustrates generally an example of a user-interchangeable flow cell compartment.

The example 400 includes a sample module 450, such as can be used to provide modular expandability and improve alignment of the optical assembly. An example of a sample module 450 holding assembly 1502 is illustrated at FIGS. 15A and 15B, and further described below.

Figure 5:
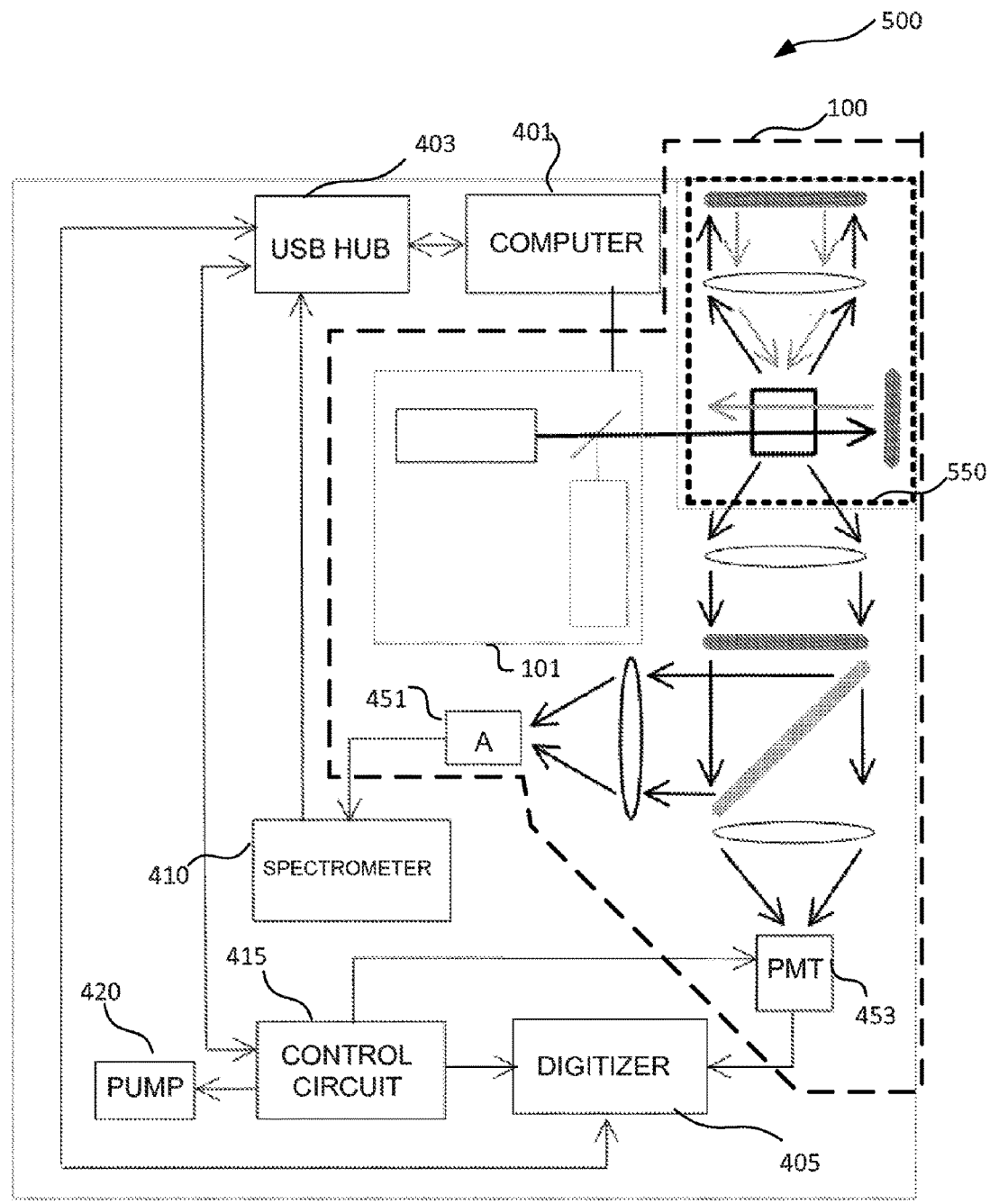
FIG. 5 illustrates generally a block diagram of an example of an optical system.
Figure 6:
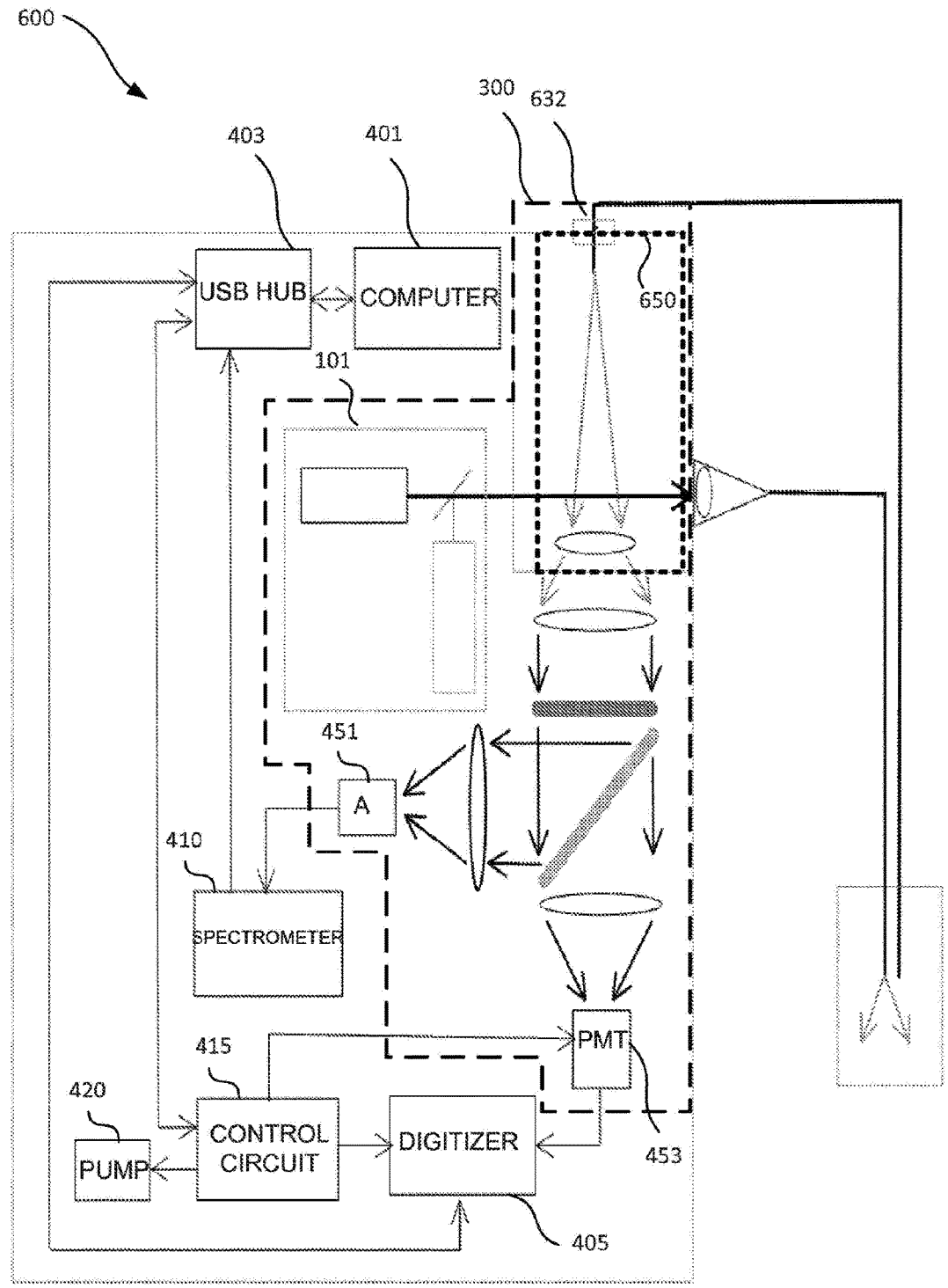
FIG. 6 illustrates generally a block diagram of an example of an optical system that includes a fiber probe.

FIGS. 5 and 6 illustrate generally block diagrams of examples 500 and 600 of other system configurations for spectral and temporal emissions analysis. The examples 500 and 600, similarly to the example 400, include the broadband spectrometer 410, the photomultiplier (PMT) 453 coupled to the waveform digitizer 405, and the control circuit 415 coupled to the computer 401 via the USB hub 403. The first optical system 100 is incorporated into the example 500, and the third optical system 300 is incorporated into the example 600. For example, the second detector 152 corresponds to the PMT 453, and the first detector 151 corresponds to the spectrometer 410 (e.g., via the spectrometer fiber coupling 451). In the examples 500 and 600, the computer 401 is coupled to the excitation module 101 of the optical system 100.

The example 500 includes a sample module 550, such as can be used to provide modular expandability and improve alignment of the optical assembly. The sample module 550 can include a liquid volume sample cell and one or more optical processing elements, such as lenses, filters, or mirrors. The example 600 includes a sample module 650, such as can be used to couple an optical fiber probe to the system, such as described above in the discussion of FIG. 3.

In an example, the sample modules 450 and 550 can include liquid-containing measurement cells (e.g., comprising a stimulated liquid volume), and can optionally be enclosed with a back-reflecting mirror (e.g., the mirror 111). In an example, flow-through measurements, such as using internal or external pumping of the analyzed liquid through the sample modules, and measurements of small sample volumes in glass or disposable plastic cells, can each be conducted using the interchangeable sample modules 450 and 550.

An accessible sample module can also provide various options for instrument tests, calibration, or sample treatment, such as before and/or during measurement, such as for any of the examples of FIGS. 4-6. For example, calibration light sources for measuring instrument spectral response can be introduced in the excitation area. In an example, phytoplankton samples can be exposed to light to cause light-adaptive changes in photosynthetic apparatuses. In an example, a light source can be mounted in a sample module instead of using a mirror.

Referring again to FIGS. 4-6, physical examples of the systems depicted in the examples 400, 500, and 600, can be arranged similarly to the block diagrams shown in the figures. In this manner, the geometry of the optical design permits a measurement area to be located in the corner of the instrument case, which can isolate a potentially wet measurement area from sensitive electronic and optical components inside the instrument case. The arrangement also simplifies instrument maintenance and provides additional options for instrument configuration.

Figure 9:
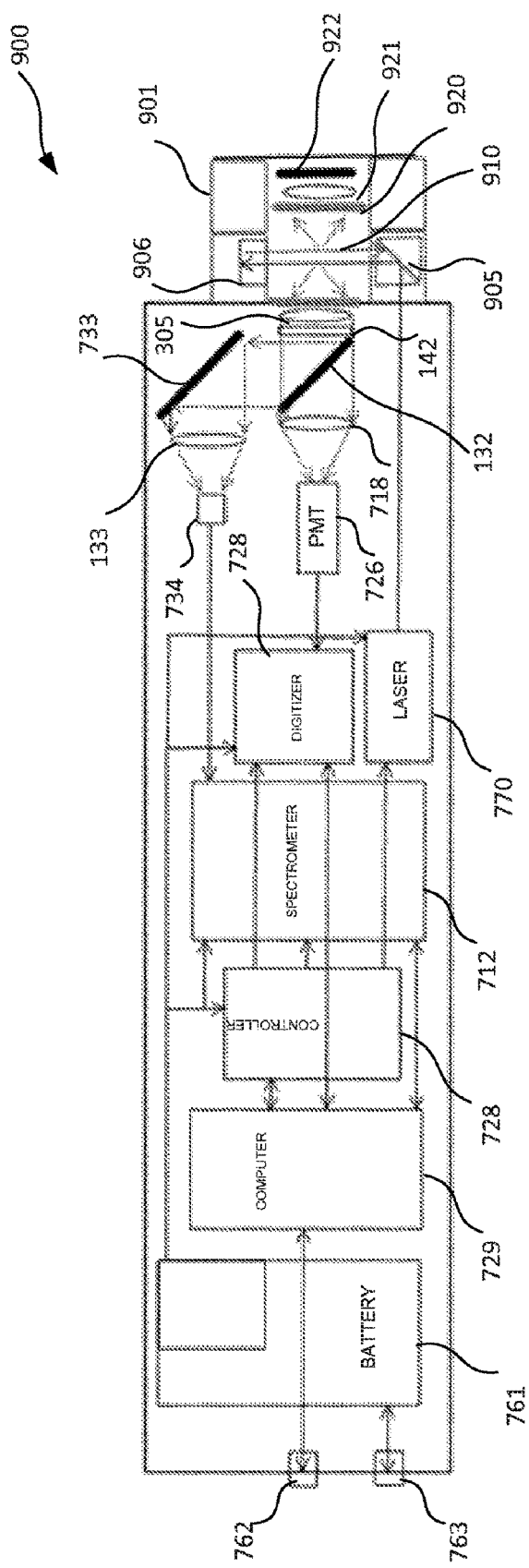
FIG. 9 illustrates generally an example of an in-situ optical system that includes discrete optical elements.
Figure 10:
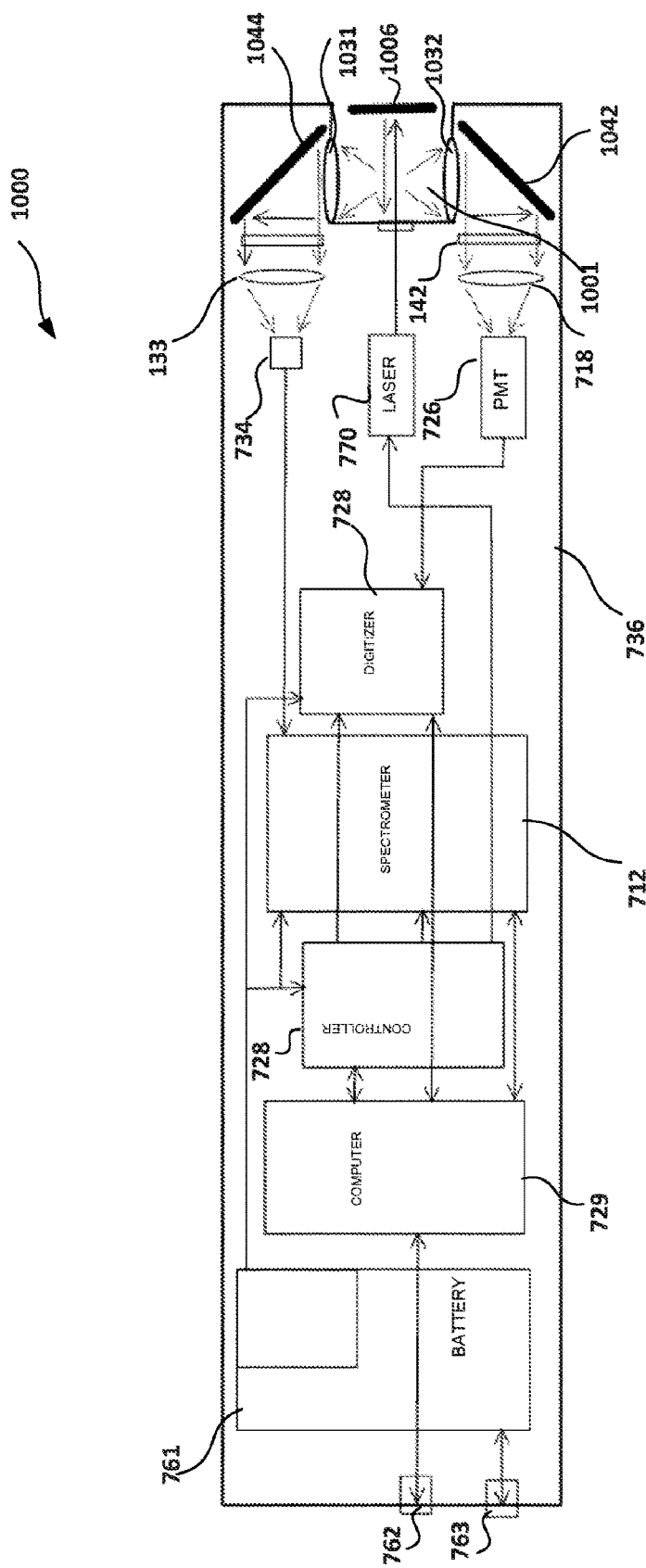
FIG. 10 illustrates generally an example of an in-situ optical system for in-situ analysis of liquids.
Figure 11:
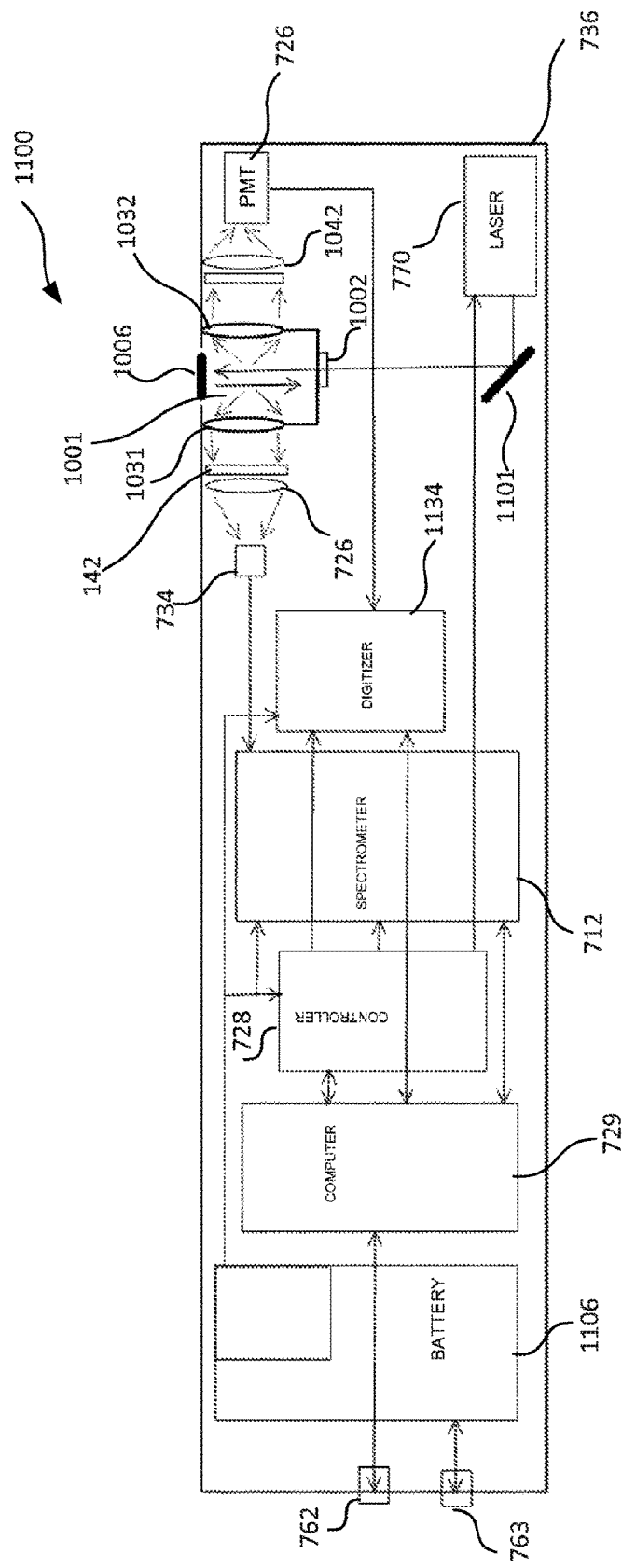
FIG. 11 illustrates generally an example of an in-situ optical system for in-situ analysis of liquids.

In an example, the various sample modules (e.g., the sample module 550) can be removable, swappable, or interchangeable. The sample modules can include flow-through or fixed-volume fluorometric cells (e.g., comprised of quartz, glass, disposable plastics, and the like) and can be configured as shown in FIGS. 9-11, among other ways. In some examples, the sample modules can include some optical components, such as include one or more mirrors or collimating lenses. In an example, swappable sampling modules can be secured in place and appropriately aligned for measurement, such as using metal rods that extend in the sample compartment from an optical cage mounting system located inside the instrument case (see, e.g., FIG. 15B).

In the example 600, the sample module 650 can include a swappable fiber-probe module (FPM) that can enable external, including remote, measurements. As described above in the discussion of FIG. 3, the FPM assembly may include a fiber probe adaptor to focus an excitation energy into an excitation leg of the fiber probe, and can include an adaptor lens to receive information from the collection leg, such as to adjust divergence of the emission outgoing from the open end of the fiber probe leg inside the FPM to ensure collimation of the emission by the receiving optics of the instrument.

In an example, the optical systems described above can provide physical isolation of a stimulated liquid volume from the electronic components (e.g., the excitation sources, the detectors/analyzers, controllers, power supplies, etc.) and most optical components. Physically isolated components can be enclosed in a liquid-proof case. In an example, the physically isolated components can be separated from a measurement area that contains a liquid sample, such as using a wall. In an example, one or more lenses or optional optical windows can be hermetically mounted to the wall to enable optical communication between the physically isolated components and the measurement area that contains a liquid sample. In an example, an optical window can be hermetically mounted to the wall. The optical window can be configured to be transparent to an excitation light source.

Figure 7:
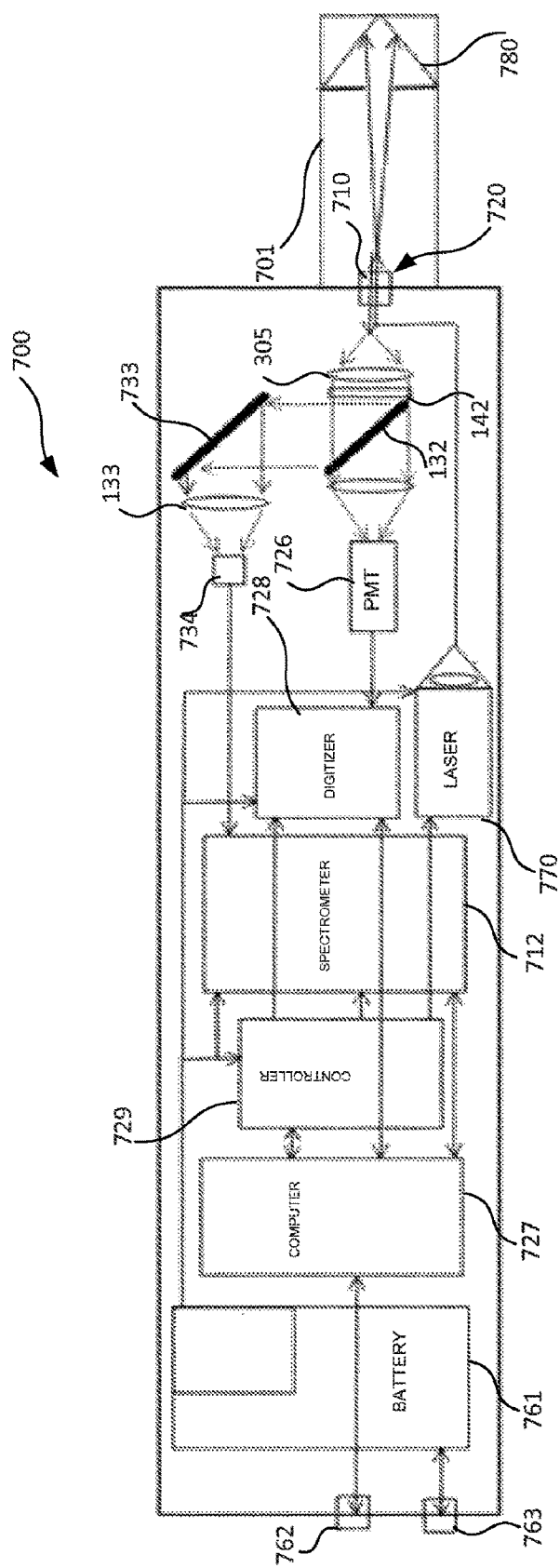
FIG. 7 illustrates generally an example of an in-situ optical system.

In an example, an optical system can be configured for in-situ measurements (e.g., the instrument can be surrounded by a liquid sample, such as water). FIG. 7 illustrates generally an example of a first in-situ optical system 700 that can be configured to conduct spectrally and temporally resolved in situ LSE measurements in a measurement chamber 701, such as using a two-leg fiber probe 720. The optical and electronic system components can be enclosed in a sealed water-proof case, such as with a port 710 provided for a tip of the fiber probe 720. A water-proof communication connector 762 and power connector 763 can be used to communicate with one or more external devices and/or to provide external power and internal battery recharge. In an example, an optional internal rechargeable battery 761 and an optional DC-DC converter can be used to provide power for all the instrument components during the autonomous operation of the system.

In an example, an excitation source 770 can include a laser. The laser can be coupled to an excitation leg of the fiber probe 720, such as via an optical collimator (e.g., using a 0.6 mm fiber). In an example, the divergent excitation beam from the laser can stimulate optical emission in a water volume adjacent to the tip of the fiber-probe 720. In an example, the excitation area or volume can be covered with a cup, such as can protect a tip of the fiber probe 720 from potential mechanical damage and can reduce an amount of ambient light that can affect the measurements. Optionally, the cup can be a copper cup to protect a tip of the fiber probe from biofouling. In an example, one or more holes can be made in the cup at various locations to permit flow into the measurement area from surrounding water. In an example, an optical light trap 780 or mask can be used, such as to reduce an amount of backscatter light from reflection of the excitation beam from the internal cup walls. In an example, a 100% reflection mirror can optionally be installed inside the cup, such as to re-direct the excitation beam back into the measurement volume adjacent to the fiber tip, such as to increase the intensity of water emission measured by the instrument. If the reflection mirror is used, the optical trap 780 can be accordingly relocated in the body of the instrument case, such as to reduce the amount of elastic scattering collected by the fiber probe 720.

In an example, an emission from a stimulated volume in the excitation area near the fiber probe 720 can be received by one or more signal fibers in the tip of the fiber probe 720 (e.g., six 0.6 mm fibers can be used). An excitation leg of the fiber probe 720 can be connected inside the instrument case to a collimating lens, such as the collimating lens 305 described above in the example of FIG. 3. The collimated emission beam can be filtered, such as by an appropriately selected filter (e.g., a long-pass filter, or the first filter 142), such as to reduce an intensity of laser elastic scattering, and can optionally be split by an optical splitter (e.g., the optical splitter 132 in the example of FIG. 3), such as an appropriately selected dichroic mirror.

In an example, a spectral portion of an emission to be temporally analyzed, such as with a desired temporal resolution, can be focused by a lens onto a photodetector, such as a photomultiplier tube 726. In an example, an electrical waveform generated by the temporal change in the detected emission signal can be quantified by a waveform digitizer 728 and transferred to an instrument computer 727, such as for processing and/or storage.

In an example, a spectral portion of an emission to be spectrally analyzed, such as over a desired spectral band, can be reflected by a mirror 733, such as a 100% mirror, that can direct the emission to a collimating lens 133 that can focus the emission into a fiber 734 connected to an input of a spectrometer 712. The measured LSE spectrum can be transmitted to the computer 727, such as for processing and/or storage. An electronic controller 728 can be used to provide an interface between the computer 727 and various instrument components. The computer 727 can issue measurement control commands interpreted and disseminated using the controller 728, such as according to one or more measurement protocols or algorithms.

Figure 8:
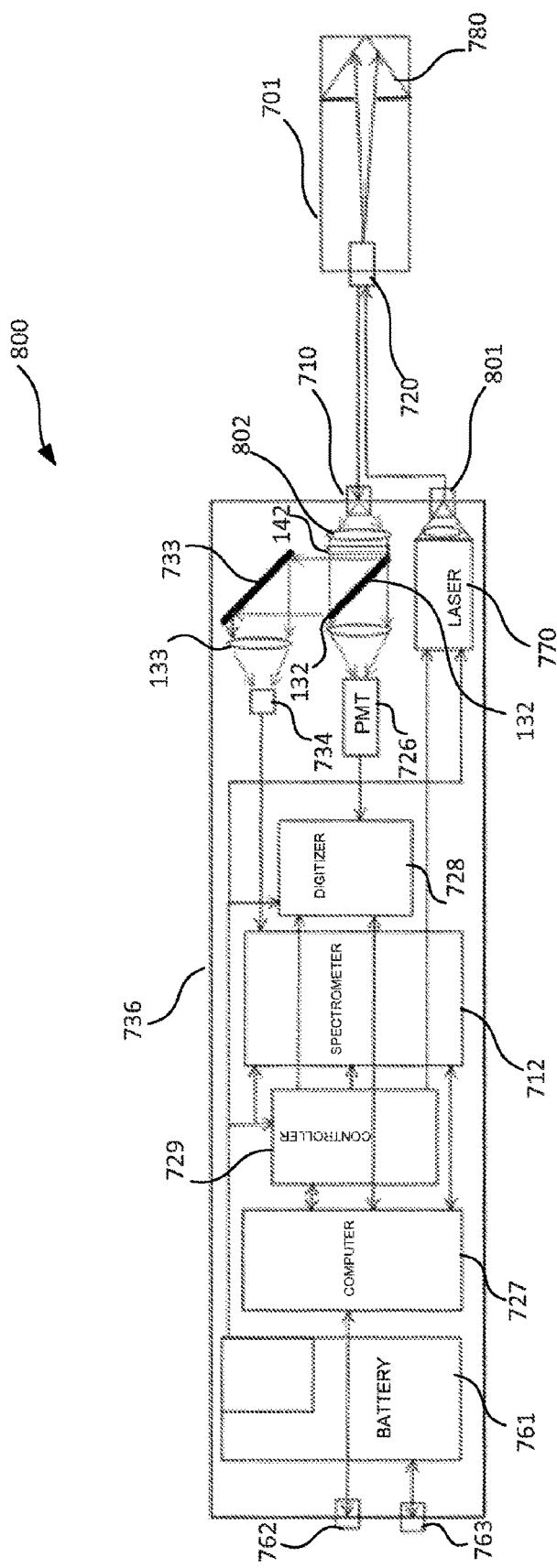
FIG. 8 illustrates generally an example of an in-situ optical system that includes a fiber probe.

FIG. 8 illustrates generally an example of a second in-situ optical system 800 that can be configured to conduct spectrally and temporally resolved in situ LSE measurements in the measurement chamber 701, such as using a two-leg fiber probe 820. The optical and electronic components of the second in-situ optical system 800 are substantially identical to those in the first in-situ optical system 700 of FIG. 7 except that the fiber probe 820 of the second in-situ optical system 800 is coupled to the instrument case using an extended fiber. That is, the fiber probe 820 can be located outside of the instrument case to permit remote measuring of LSE within the measurement chamber. The excitation and signal legs of the fiber probe 820 can be connected to a laser-fiber coupling adaptor 801 and a collimating adaptor 802, respectively, such as via corresponding fiber connector ports mounted on the panel of the instrument case. The length of the fiber probe 820 can be selected with regard to the specific instrument application and can vary from several centimeters or less to several hundred meters or more. In an example, the measurement chamber can be inserted into a liquid volume to be analyzed and filled with the liquid, such as via appropriately located holes in the measurement chamber body, as described above in the discussion of FIG. 7.

In an example, a bench-top or wall-mounted instrument configuration can be implemented using the second in-situ optical system 800, such as with the extended external fiber probe 820 inserted in a container filled with a liquid sample to be concurrently temporally and spectrally resolved using LSE measurements of the sample. In an example, such an instrument configuration can be used for optical analysis of liquids in sample tubes or bottles located on a laboratory bench or in a motorized carousel, while the fiber probe measurement chamber can be mounted on a motorized arm to automatically insert the measurement chamber into and/or remove the measurement chamber from the sample volume to be measured.

In an example, an instrument configuration implemented using the second in-situ optical system 800 can be used for continuous underway measurements of horizontal distributions of LSE characteristics, such as for use on a stationary or moving research vessel. The instrument case can be mounted at an appropriate location and can optionally be connected to an external monitor or computer, such as via a communication port, such as to provide real-time display of the measurements and/or data storage and processing. On a small vessel or motorboat, the measurement chamber of the fiber probe 820 can be mounted on an appropriately designed holder that can be directly inserted in the water from the boat, such as to provide for the continuous underway in situ measurements, such as without requiring use of a pump for sampling. On a larger vessel, the fiber probe can be mounted to keep the measurement chamber in a small container continuously filled with the water provided by a shipboard sampling pump.

In an example, an instrument configuration implemented using the second in-situ optical system 800 can be used to configure a compact, robust laser fluorometer, such as for deployment from one or more stationary platforms (e.g., oil or oceanographic platforms, buoys, moorings, etc.). A waterproof instrument case can be securely mounted on the platform, while the fiber probe 820 can be submerged in the water. LSE information can be locally analyzed or transmitted (e.g., wirelessly) to a central analysis computer. In an example, the instrument can be powered by an external solar panel, such as to provide long-term measurements that can be trended over time.

In an example, an instrument configuration implemented using the second in-situ optical system 800 can be used as a portable, over-the-shoulder instrument with the fiber probe 820 on a handheld implement that can be used for fast, real-time field tests and measurements in research and environmental studies.

In an example, the in-situ optical system 800 includes, among other components, the laser 770 (e.g., World Star Tech TECGL-35G-515-SMA-TTL-A, 35 mW at 518 nm), the spectrometer 712 (e.g., Ocean Optics USB4000), the photomultiplier (PMT) 726 (e.g., Hamamatsu H10720), the waveform digitizer 728 (e.g., ChronoLogic CL4000; 14-bit 100 MS/s), the USB controller 729 (LabJack U3-LV; turns the laser On/Off and triggers the waveform digitizer via TTL; controls the PMT gain via analog output in 0.5-1.1 V range), and the computer 727 (e.g., CompuLab fitPC2i; runs LabView script under Windows 7). In an example, the optical components can include a dual-leg fiber probe (e.g., Ocean Optics R600-7-VIS-125F; excitation via a 0.6 mm optical fiber; LSE collection via six 0.6 mm optical fibers), a long-pass filter (LFP) (e.g., Semrock FF-515/LP-25), a dichroic beam splitter (e.g., Semrock FF677-Di01-25x36) in a cube filter mount (e.g., Thorlabs CM1-DCH), a lens (e.g., Thorlabs LA1951-A), collimating lenses (e.g., Thorlabs F810SMA-543), a 90-degree steering mirror cube (e.g., Thorlabs CM1-EO2) attached to CM1-DCH via mounting bracket (e.g., Thorlabs CM1-CC), and a fiber (e.g., Thorlabs FH 22-910-CUSTOM). The instrument can be powered via AC-DC adaptors, however a set of 12 V lithium-ion rechargeable batteries (e.g., Super Circuits MVLBCS-7), such with a 12-5 V DC-DC converter (e.g., Traco Power TEL20-1211), can be used for autonomous operation of the instrument. For evaluation, a spectrometer with a TE-cooled CCD sensor (e.g., BWTek BT112E) can be used, and a 405 nm, 18 mW laser (e.g., World Star Tech TECBL-18G-405-TTL) can be coupled to the fiber via a collimator (e.g., Thorlabs F810SMA-543).

A feature of this instrument configuration can be the use of a dichroic LSE beam splitter (see, e.g., dichroic 132 in FIGS. 3 and 7) that can include a specific transient characteristic that allows passing about 50% of Chl-a fluorescence signal through the filter while reflecting about 50% of Chl-a fluorescence along with 100% of the LSE signal collected in the visible spectral portion outside of the Chl-a fluorescence band (i.e., 400-665 nm). The reflected LSE portion can be directed for the spectral analysis, while the passed Chl-a fluorescence can be used for temporarily-resolved measurements of Chl-a fluorescence induction to retrieve the magnitude of variable fluorescence. Fv/Fm for phytoplankton photo-physiological assessments.

Referring now to FIG. 9, an example of a modified optical configuration 900 is shown. The modified optical configuration 900 can be used to conduct spectrally and temporally resolved LSE measurements in a measurement chamber 901 via an optical window 902, such as using discrete optics instead of a fiber probe. The measurement chamber 901 can serve to reduce an amount of ambient light in the excitation area 910 filled with the liquid sample. An excitation energy can be delivered to the measurement chamber 901 either directly (e.g., not shown in the example of FIG. 9), or the excitation energy can be delivered to the measurement chamber via a 100% reflecting 90-degree mirror/prism 905. The excitation energy can optionally be reflected back by a 100% mirror 906, such as to increase the intensity of excitation. A laser-stimulated emission (LSE) can be collected from the contents of the excitation area 910, such as via the sealed optical window 902, and can be collimated by a lens 305. An amount of collected emission can be enhanced (e.g., up to two-fold) such as by using an optional optical assembly, which can be attached to the measurement chamber 901 and can include a sealed optical window 920, a lens 921 that collects and collimates the LSE from the excitation area, and a 100% flat mirror 922 that reflects the collected LSE back to the excitation area. Other components of the modified optical configuration 900 can be similar to the respectively marked components displayed in the examples of FIGS. 7 and 8.

In an example, the modified optical configuration 900 can be used for in-situ measurements when the measurement chamber 901 or the entire instrument case is submerged in the liquid to be analyzed (e.g., water). Appropriately located holes in the measurement chamber 901 body can provide access for the sampled water to seep inside the measurement chamber. This system configuration can also be used to configure a bench-top or wall-mounted instrument for LSE measurements in a flow-through or discrete sample cell to be inserted in the excitation area in the measurement chamber 901.

As an example of practical implementations of the systems and configurations described above, any of the configurations can be used to configure an instrument for Advanced Laser Fluorescence (ALF) analyses of natural aquatic environments, such as using the general approach and measurement protocols described in Chekalyuk, PCT Patent Publication WO 2011/069067.

FIG. 10 illustrates generally an example 1000 of a modified optical configuration. The example 1000 can be used to conduct spectrally and temporally resolved LSE measurements in a measurement chamber 1001 via an optical window 1002, such as without use of a fiber probe. In an example, the optical system used to excite the contents of the measurement chamber 1001 and receive emissive information from the contents of the measurement chamber 1001 can correspond to the optical system 200. For example, the filters 1042 and 1044 can correspond to the filters 242 and 244, respectively, however the filter 1042 and 1044 can be 45 degree mirrors, such as with or without spectral filtration. In an example, an excitation energy can be delivered to the measurement chamber 1001 either directly or via a 100% reflecting mirror 1006. A laser-stimulated emission (LSE) can be collected from the contents of the measurement chamber 1001, such as via the sealed lenses 1031 and 1032, and can be collimated and/or focused by respective lenses 1016 and 1042. Using the filters 1042 and 1044 as 45 degree mirrors to redirect the optical path back toward the source can yield a more compact instrument configuration.

FIG. 11 illustrates generally an example 1100 of a modified optical configuration that is similar to the example 1000. The example 1100 can include a single 45 degree mirror 1101 between the source 770 and the measurement chamber 1001, and can omit the 45 degree mirrors between the detectors 726 and 734 and the measurement chamber 1001. In this manner, the example 1100 can yield a smaller instrument cross-section compared to the example 1000.

Figure 12:
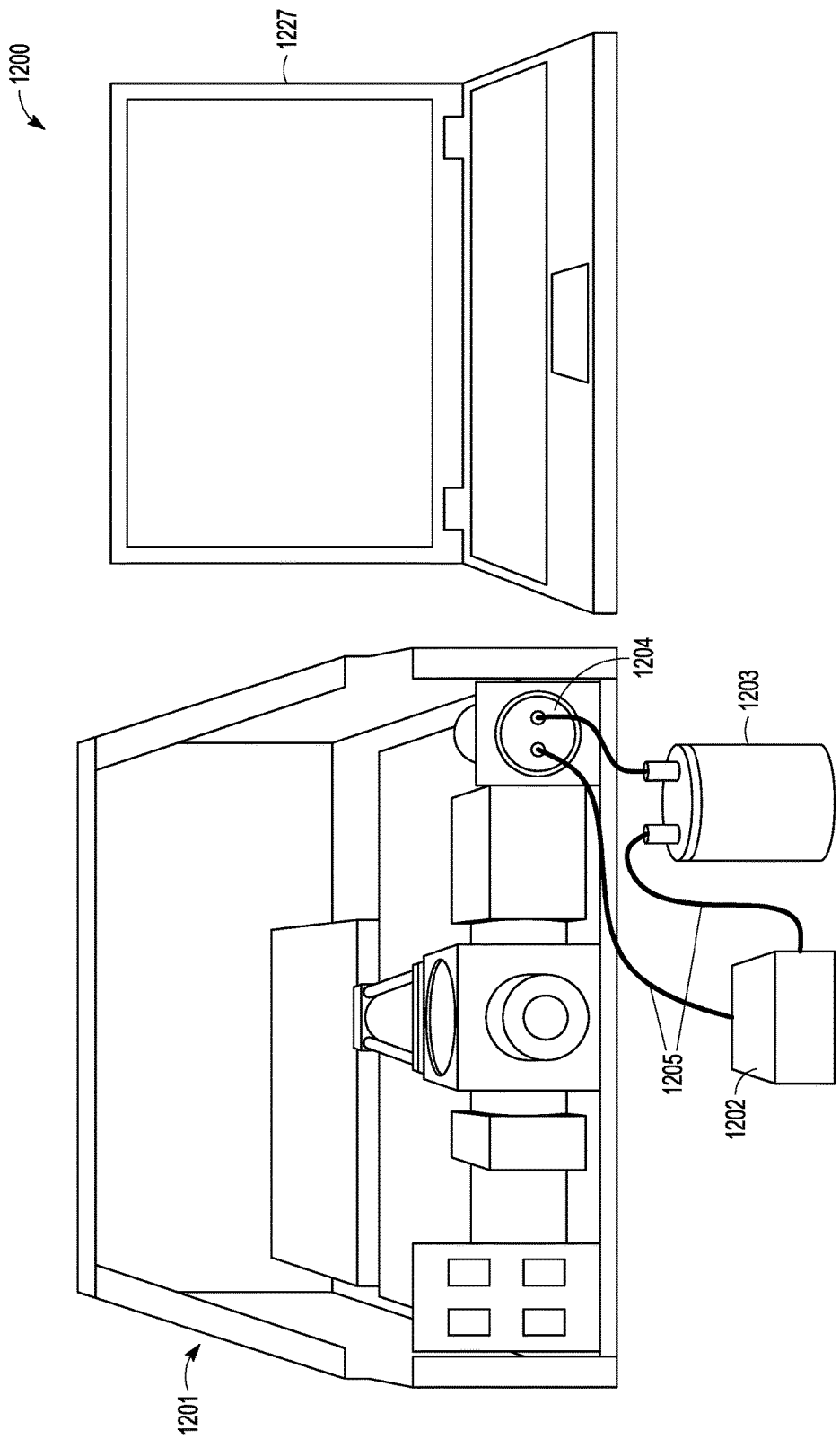
FIG. 12 illustrates generally an example of an optical analysis system that includes a computer.

FIG. 12 illustrates generally an example of an optical system 1200, such as corresponding to the instrument configuration example of FIG. 4. The optical system 1200 includes a computer 1227 coupled (e.g., via USB) to an excitation/detection module 1201. The excitation/detection module 1201 can include, for example, any one or more of the components described above in the discussion of FIGS. 1-11. For example, the emission/detection module 1201 can include a configuration that corresponds to the example 900. The emission/detection module 1201 can include a user-interchangeable sample cell 1202, such as can be physically coupled to a sample volume container 1203 via a pump 1204 and/or one or more fluid tubes 1205.

In an example, the optical system 1200 can be used to measure phytoplankton pigment fluorescence, such as in a liquid volume in the sample volume container 1203, such as for assessment of phytoplankton biomass, community composition, or photo-physiological status (via measurements of variable fluorescence. Fv/Fm). In an example, the optical system 1200 can be used to assess a concentration of chromophoric dissolved organic matter (CDOM) in a water sample. Water Raman scattering or elastic scattering of laser excitation can be measured using the optical system 1200, such as along with fluorescence spectral bands.

The optical system 1200 can include a single laser (e.g., 514 nm) for excitation of natural water samples. The optical system 1200 can be used for broadband spectral measurements of fluorescence and water Raman scattering, such as using a spectrometer to and processor to conduct spectral deconvolution analysis of spectral information received from the sample in response to stimulation of the sample using the laser. In an example, the fluorescence constituents present in the sample can be identified. In an example, the 670-700 nm range of LSE can be used for temporally resolved measurements of fluorescence induction, such as using a photomultiplier or a waveform digitizer to assess phytoplankton photo-physiological status (see. e.g., FIGS. 1-11).

Figure 13:
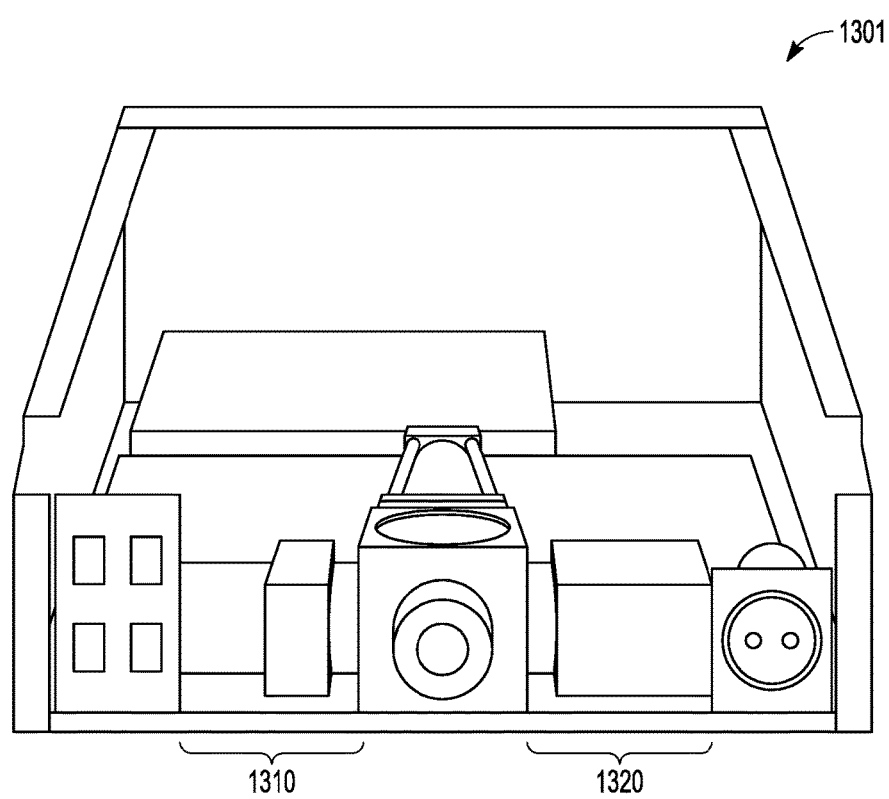
FIG. 13 illustrates generally an example of a dual-channel optical system.

FIG. 13 illustrates generally an example of an emission/detection module 1301 that can include two optical channels for collection of laser-stimulated emissions (LSE), such as corresponding to the optical systems 200 and 400 described above. The optical channels can include respective detectors configured to detect emissions in the respective first and second spectral ranges comprising about 500-800 nm and about 670-700 nm. In the example of FIG. 13, a removable, user-interchangeable compartment for sample analysis can be inserted in the area of excitation. In an example, the optical system 1300 can be configured to enclose several instrument components in a waterproof enclosure, such as for in-situ measurements.

In an example, one or more one more steering mirrors (e.g., 100% steering mirrors) can be included in the excitation/detection module 1301 to rotate (e.g., about 90 degrees) an optical axis of a first-side collection/filtration channel 1310 to make the optical axis parallel to the laser excitation source (see, e.g., FIG. 10). In an example, a second-side collection/filtration channel 1320 can be similarly configured to redirect an optical emission. In an example, the various electronic components comprising the excitation/detection module 1301, such as including a compact computer controller or a battery (see, e.g., FIGS. 7-11), can be aligned along the optical axis of the laser.

In the example of FIG. 13, achromatic doublets can be used as one or more lenses to ensure broadband (e.g., 500-800 nm) emission measurements. A high-quality long-pass filter (e.g., at about 520 nm) and band-pass filter (e.g., centered at about 685 nm, such as with 25 nm bandwidth) can be used.

In the example of FIG. 13, one or both of a spectrometer and a control computer can be provided externally to the excitation/detection module 1301. In an example, one or both of the spectrometer and the control computer can be connected to the excitation/detection module 1301 using waterproof connectors and cables, such as waterproof USB or waterproof optical fiber connectors and cables.

Figure 14:
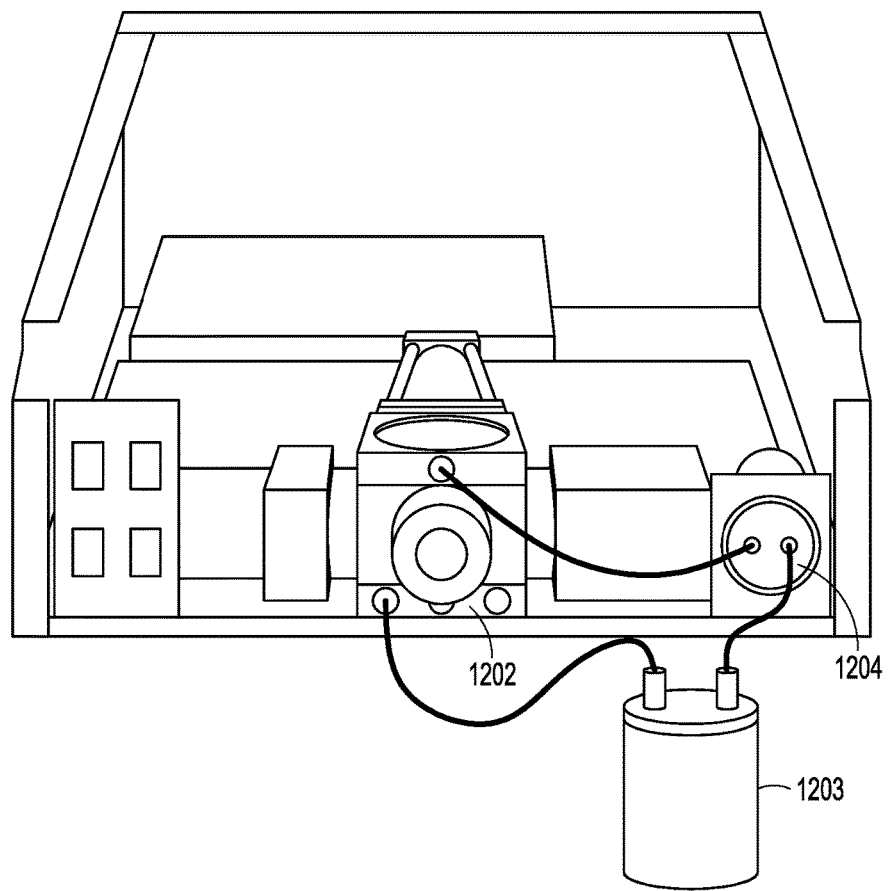
FIG. 14 illustrates generally an example of a flow cell measurement module.

FIG. 14 illustrates generally an alternative view of the emission/detection module 1201 of FIG. 12, such as with the user-interchangeable sample cell 1202 secured into a measurement zone of the instrument. In an example, the user-interchangeable sample cell 1202 is a user-interchangeable flow-through cell coupled to the sample volume container 1203 and the pump 1204. One or more other sample volume containers (not shown) can be optionally coupled to the user-interchangeable sample cell 1202.

FIG. 15A illustrates a top view of a user-interchangeable flow cell compartment 1501 secured to a holding assembly 1502. FIG. 15B illustrates the holding assembly 1502, which is generally configured to hold a portion of interest of the interchangeable flow cell compartment 1501 within the excitation area. For example, the portion of interest of the interchangeable flow cell compartment 1501 can be the sample cell 112 (not visible in the illustrations of the examples of FIGS. 15A and 15B). In an example, the interchangeable flow cell compartment 1501 comprises a vertical 4 mL flow cell compartment enclosed in a black anodized cube compartment (see, e.g., FIG. 15A). The vertical compartment can have holes in its body, such as can be configured to slide the vertical compartment in the excitation area along four (e.g., or more, or fewer) corresponding metal rods of the holding assembly 1502, such as rods that extend into the excitation area from a laser mounting 1505 (see, e.g., FIG. 15B). In an example, the compartment for sample analysis can be a disposable compartment. In an example, a disposable compartment can omit a metal cover to provide access to the cell. Filling a measurement cell with a liquid sample can be performed using an automatic pipette, or optionally by partially removing the measurement cell from the compartment along the metal rods.

In an example, the user-interchangeable flow cell compartment 1501 can include one or more of (1), a disposable cell compartment, (2) a funnel cell compartment, (3) a flow-through cell compartment, or (4) a self-pumping flow-through cell compartment. A disposable cell compartment can be used with one or more of the optical systems described in FIGS. 1-11, such as disposed proximal to the mirror 111 of the optical system 100. In an example, a funnel cell compartment can be used. An input to the funnel cell can be configured to receive a liquid sample. An output from the funnel cell can be configured with a manual or automatic clamp, such as a solenoid clamp. Distal to the optional clamp, a tube can carry a liquid sample into, e.g., the sample module 110, for analysis. In an example, a flow-through cell compartment can be used (see. e.g., FIG. 14). Connectors for a flow-through cell compartment can be positioned on a common, horizontally-extended plate, such as to evenly distribute an insertion force. A liquid sample can flow into a sample module 110 via an input connection, or the liquid sample can exit the measurement cell area via an output connection. In an example, a self-pumping flow-through cell compartment can be used. In an example, a manual or automatic pump can be provided to draw a liquid sample from an external source through a measurement cell area, such as via an input connection (see, e.g., FIG. 14).

Figure 16:
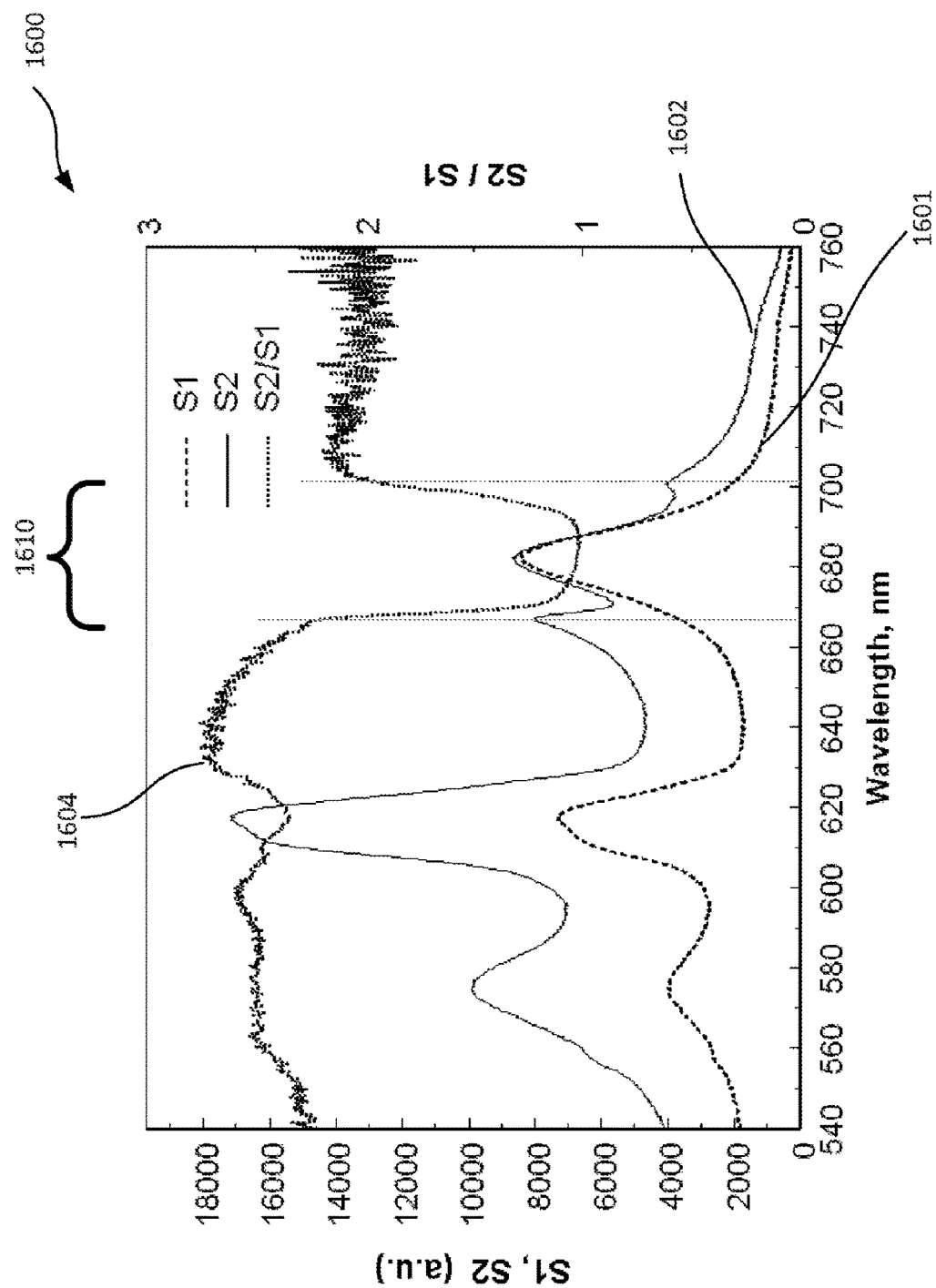
FIG. 16 illustrates generally an example of a comparison of spectral measurements.

FIG. 16 illustrates generally an example 1600 of a spectral measurement of phytoplankton pigment fluorescence, such as measured using one of the optical systems described above in the discussion of FIGS. 1-11. In the example of FIG. 16, a spectrum 1601 can represent a measurement by the optical system 400, such as using a 90-degree optical scheme, such as without using the emission enhancement provided by back-reflection of the red, band-pass interference filter 244 (see, e.g., FIGS. 2 and 4). A spectrum 1602 represents a measurement by the optical system 400 when the enhancement is used. As shown, the intensity of the measurement by the optical system 400 with the enhancement module 120 can result in about a two-fold increase in intensity throughout the spectral range, such as except for a spectral range of a transparency window 1610 (e.g., corresponding to the red filter 244; see FIGS. 2 and 4). A relative spectrum 1604 illustrates a ratio of intensities of the spectra 1602 and 1601 (e.g., spectrum 1602/spectrum 1601; see right vertical axis for scale). A correction function is represented by the line 1604, which can be used to correct spectral measurements conducted with unblocked back reflection for the signal drop in the spectral range of a red filter transparency window 1610. As illustrated, back reflection from one or more filters (e.g., the mirror 122 in the example of FIG. 1) can improve spectral measurements by increasing the signal intensity by about 2.14 times over a broad spectral range, such as outside of the transparency window 1610 (667-707 nm) of the red filter 244 (see, e.g., FIGS. 2 and 4).

Figure 17A:
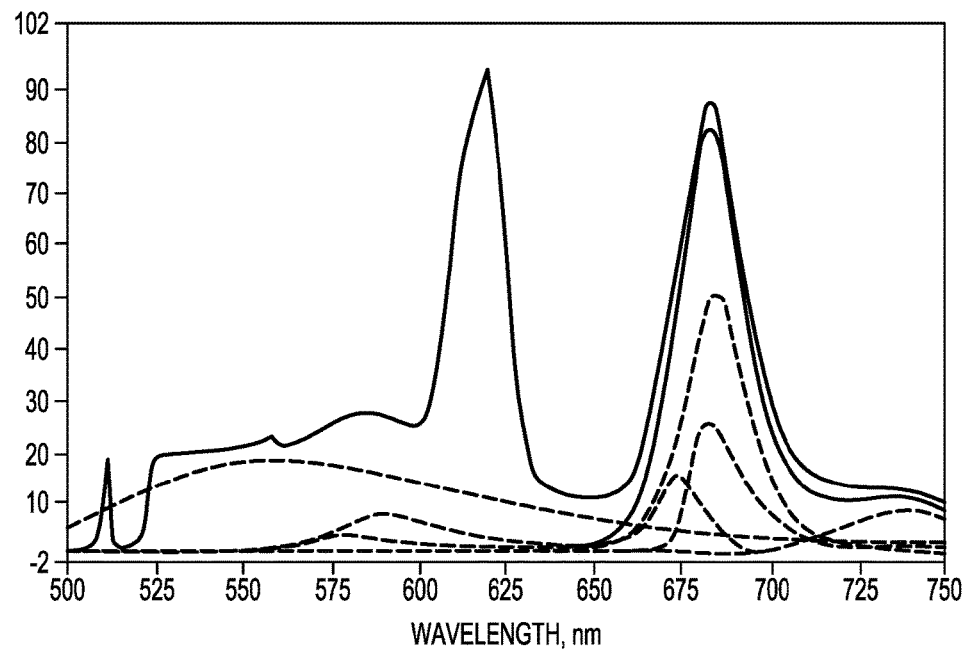
FIG. 17A illustrates generally an example of a spectrally-resolved emission measurement of pigment fluorescence using a fiber probe.
Figure 17B:
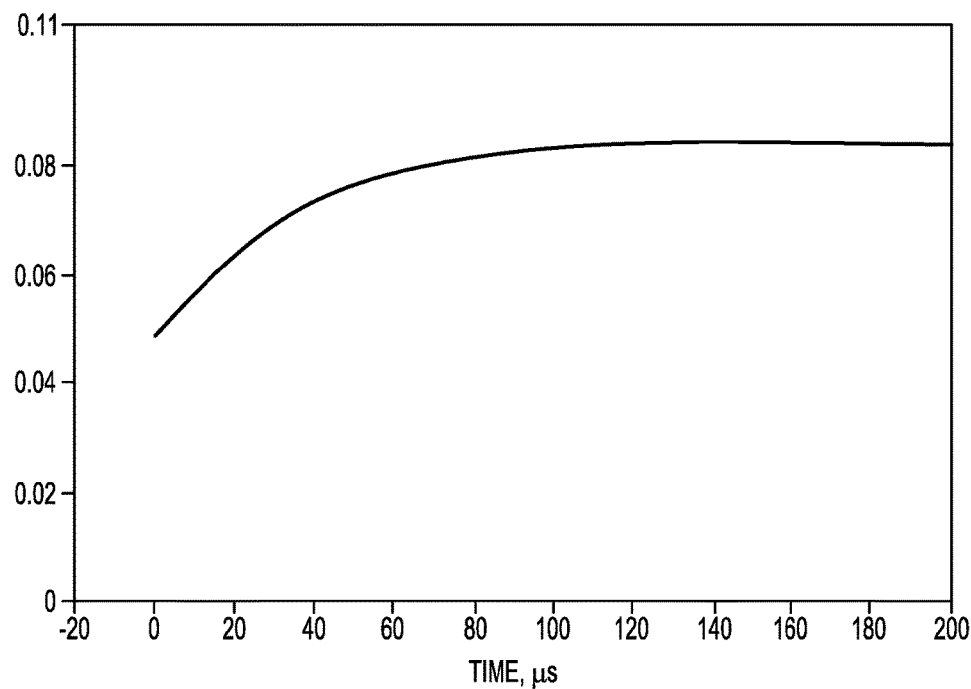
FIG. 17B illustrates generally an example of a temporally-resolved emission measurement of pigment fluorescence using a fiber probe.

An example of spectrally and temporally resolved fiber-probe measurements with a 514 nm laser excitation using, e.g., one or more of the systems shown in the examples of FIGS. 3, 6, and 8, in the phytoplankton culture of Cryptophytes (Cr) diluted to natural concentration typical for estuarine waters is shown in the examples of FIGS. 17A and 17B. For example, FIG. 17A illustrates an LSE spectrum for the fluorescence bands typically observed in natural waters containing Cryptophytes, including a tail of the laser elastic scattering (around pixel 800), a Cr-specific band of phycoerythrin fluorescence peaking at 590 nm (around pixel 1150), a strong peak of water Raman scattering (around pixel 1400), and a Chl-a fluorescence band peaking around pixel 1600 (e.g., partially cut by the dichroic filter in the example of FIG. 17A). This spectrum can be corrected for the spectral characteristics of the dichroic filter and the spectrometer spectral response and used for spectral deconvolution (SDC) analysis, such as described in Chekalyuk, PCT Patent Publication WO 2011/069067. In the example of FIG. 17B, a Chl-a fluorescence induction curve measured by a PMT and waveform digitizer is shown. Time is displayed along the horizontal scale. In this example, a duration of the laser excitation flash was about 200 microseconds, and the fluorescence induction was observed over about 100 microseconds (e.g., an optimal time scale for photo-physiological assessments).

In the example of FIG. 17A, the spectral integration time of 3 seconds yields high-quality spectral measurements. Spectral measurements at shorter integration times still yield an acceptable signal/noise (S/N) ratio for accurate fluorescence assessments using the SDC analytical algorithms in Chekalyuk. The Chl-a induction illustrated in FIG. 17B was averaged over 10 laser shots at about 10 Hz repetition rate (e.g., corresponding to 1 second total measurement time). Laboratory tests have shown that even single-shot time-resolved measurements can yield acceptable S/N ratio for accurate assessment of variable fluorescence, Fv/Fm.

Factors for selecting components for instruments corresponding to the emission/detection systems described herein include, among others, component dimensions and power consumption. A design objective in developing such an instrument can be long-duration autonomous operation via battery power. An important component to meet these criteria is the computer. In an example, a fitPC2i can be used because it has a uniquely small form factor (10×11 cm) and low power consumption (6 W), such as while running a full-functioning operating system (e.g., Windows 7). Using such a computer, it can be feasible to pack an instrument corresponding to one or more of the FIGS. 1-11 in a tube having an internal diameter of about 12.5 cm and a length of about 50 cm length. A simplified, but fully functional version of the ALF software can be used to provide instrument operation under control of the lower-power compact computer.

In sum, this document describes, among other things, (i) a new system configuration that can incorporate a single source of optical excitation and single optical collector of emission stimulated in a liquid volume of interest. Both a fiber probe and/or discrete optics can be used to deliver an excitation energy (e.g., provided by a collimated laser emission) to the liquid volume of interest, and to collect stimulated emissions from the liquid volume. In an example, a dichroic splitter at the output of the optical collector can direct specific spectral portions of LSE to the respective sensors conducting temporally and spectrally resolved LSE measurements. This can provide an instrument that is easier to implement and maintain, since the measurements can be conducted via a small tip of a fiber probe, or via a single optical window. Such arrangements can make possible various technological applications, including in situ combined spectrally and temporally resolved measurements from various platforms (including autonomous unmanned vehicles), fiber-probe sample analysis (including portable, over-the-shoulder field instruments), or fiber-probe underway measurements using various ships, small vessels and motorboats, etc. Applications can include, for example, analytical instrumentation for aquatic research and environmental monitoring, chemistry, medicine, pharmaceutical manufacturing, or food manufacturing.

VARIOUS NOTES & EXAMPLES

Each of the following non-limiting examples can stand on its own, or can be combined in various permutations or combinations with one or more of the other examples.

Example 1 can include or use subject matter such as an excitation and optical emission detection system, such as can include or use an excitation module, including one or more electromagnetic emission sources, the one or more emission sources configured to provide a collimated excitation energy to stimulate a liquid sample and evoke an optical emission from the liquid sample, and a first mirror configured to receive at least a portion of the excitation energy, after the excitation energy stimulates the liquid sample, wherein the first mirror can be configured to reflect the same or a different portion of the received excitation energy to stimulate the same or different portion of the liquid sample. Example 1 can include a first collimating lens configured to receive a first emission from the liquid sample and in response to pass a first collimated emission, a second mirror configured to receive the first collimated emission and in response to reflect at least a portion of the first collimated emission through the first collimating lens toward the liquid sample. Example 1 can include a second collimating lens configured to receive a second emission from the liquid sample and from at least a portion of the first collimated emission, the second collimating lens configured to pass a second collimated emission comprising a combination of the second emission from the liquid sample and the first collimated emission. Example 1 can include a first focusing lens configured to receive the second collimated emission and in response to pass a first focused emission, and a first emission detector configured to receive the first focused emission.

Example 2 can include, or can optionally be combined with the subject matter of Example 1 to optionally include a first spectral filter configured to receive the second collimated emission and in response to pass a filtered emission to the first focusing lens. In Example 2, the filtered emission can have reduced spectral content compared to the received second collimated emission.

Example 3 can include, or can optionally be combined with the subject matter of one or any combination of Examples 1 or 2 to optionally include a second emission detector and a second mirror. In Example 3, the second mirror can be disposed between the second collimating lens and the emission detector, and the second mirror can be configured to pass a first portion of the second collimated emission toward the first emission detector. In Example 3, the second mirror can be configured to deflect a second portion of the second collimated emission toward the second emission detector.

Example 4 can include, or can optionally be combined with the subject matter of Example 3 to include the second mirror, wherein the second mirror can include a dichroic filter configured to pass a first spectral band of the second collimated emission toward the first emission detector. In Example 4, the second mirror can be configured to deflect a second spectral band of the second collimated emission toward the second emission detector.

Example 5 can include, or can optionally be combined with the subject matter of one or any combination of Examples 3 or 4 to include the second mirror, wherein the second mirror includes a broadband beam-splitting filter that can be configured to pass like spectral information about the second collimated emission toward the first and second emission detectors.

Example 6 can include, or optionally can be combined with the subject matter of one or any combination of Examples 3-5 to include the first and second emission detectors, wherein one of the first and second emission detectors can be configured to detect spectral emission response information using the second collimated emission. In Example 6, the other of the first and second emission detectors can be configured to detect temporal emission response information using the second collimated emission. In Example 6 the detected spectral emission response information and the detected temporal emission response information can correspond to different spectral ranges.

Example 7 can include, or optionally can be combined with the subject matter of one or any combination of Examples 3-5 to include the first and second emission detectors, wherein one of the first and second emission detectors can be configured to detect spectral emission response information using the second collimated emission. In Example 7, the other of the first and second emission detectors can be configured to detect temporal emission response information using the second collimated emission. In Example 7, the detected spectral emission response information and the detected temporal emission response information correspond to the same spectral range.

Example 8 can include, or optionally can be combined with the subject matter of one or any combination of Examples 3-5 to include, as one of the first and second emission detectors, at least one of a photomultiplier or photodiode configured to detect temporal emission response information about the liquid sample. In Example 8, the other of the first and second emission detectors can include a spectrometer configured that can detect spectral emission response information about the liquid sample.

Example 9 can include, or optionally can be combined with the subject matter of one or any combination of Examples 3-5 to include the first and second emission detectors, wherein the first and second emission detectors can include at least one of a photomultiplier or photodiode. In Example 9, the first and second emission detectors can be configured to detect temporal emission response information from the liquid sample. In Example 9, the temporal emission response information detected by the first and second emission detectors can correspond to the same or different temporal ranges.

Example 10 can include, or optionally can be combined with the subject matter of one or any combination of Examples 3-5 to include the first and second emission detectors, wherein the first and second emission detectors can include a spectrometer configured to detect spectral emission response information from the liquid sample.

Example 11 can include, or optionally can be combined with the subject matter of one or any combination of Examples 3-5 to include a processor circuit, wherein one of the first and second emission detectors can include a photomultiplier or photodiode configured to detect temporal emission response information from the liquid sample. In Example 11, the other of the first and second emission detectors can include a spectrometer configured to detect spectral emission response information from the liquid sample. In Example 11, the processor circuit can be configured to use the spectral emission response information from the liquid sample to identify a spectral characteristic of the optical emission from the liquid sample, and can be configured to use the temporal emission response information from the liquid sample to identify a temporal characteristic of the optical emission from the liquid sample.

Example 12 can include, or optionally can be combined with the subject matter of Example 11 to include the processor circuit, wherein the processor circuit can be configured to use the identified spectral characteristic of the optical emission from the liquid sample to determine at least one of a phytoplankton pigment biomass, a phytoplankton community structure, a chromophoric dissolved organic matter content, or an oil content, in the liquid sample.

Example 13 can include, or optionally can be combined with the subject matter of one or any combination of Examples 11 or 12 to include the processor circuit, wherein the processor circuit can be configured to use the identified temporal characteristic of the optical emission from the liquid sample to determine a magnitude of a chlorophyll-a fluorescence induction.

Example 14 can include, or optionally can be combined with the subject matter of Example 13 to include the processor circuit, wherein the processor circuit can be configured to use the determined magnitude of the chlorophyll-a fluorescence induction to identify at least one of a photophysiological status or a photochemical efficiency of phytoplankton.

Example 15 can include or use subject matter such as an excitation and optical emission detection system, such as can include or use an excitation module, including one or more electromagnetic emission sources, the one or more emission sources configured to provide a collimated excitation energy to stimulate a liquid sample and evoke an optical emission from the liquid sample, and a first mirror configured to receive at least a portion of the excitation energy, after the excitation energy stimulates the liquid sample, wherein the first mirror can be configured to reflect the same or a different portion of the received excitation energy to stimulate the same or different portion of the liquid sample. Example 15 can include a first collimating lens configured to receive a first emission from the liquid sample and in response to pass a first collimated emission, a first optical interference filter that can have a first transparent band, the first optical interference filter configured to receive the first collimated emission and in response to pass a portion of the first collimated emission corresponding to the first transparent band, wherein the first optical interference filter can be configured to reflect another portion of the first collimated emission, not corresponding to the first transparent band, back toward the first collimating lens. Example 15 can include a first emission detector that can be configured to receive the passed portion of the first collimated emission corresponding to the first transparent band and a second collimating lens configured to receive a second emission from the liquid sample and at least a portion of the reflected first collimated emission not corresponding to the first transparent band of the first optical interference filter, wherein the second collimating lens can be configured to pass a second collimated emission comprising a combination of the second emission from the liquid sample and the portion of the reflected first collimated emission not corresponding to the first transparent band of the first optical interference filter. Example 15 can include a second emission detector configured to receive the second collimated emission comprising the combination of the second emission from the liquid sample and the portion of the reflected first collimated emission not corresponding to the first transparent band of the first optical interference filter.

Example 16 can include, or optionally can be combined with the subject matter of Example 15 to include a first focusing lens configured to receive the passed portion of the first collimated emission, corresponding to the first transparent band, and in response to pass a first focused emission toward a photo-sensitive region of the first emission detector. Example 16 can include a second focusing lens configured to receive the passed second collimated emission, not corresponding to the first transparent band, and in response to pass a second focused emission toward a photo-sensitive region of the second emission detector,
wherein the first emission detector can be configured to receive the first focused emission, and wherein the second emission detector can be configured to receive the second focused emission.

Example 17 can include, or optionally can be combined with the subject matter of one or any combination of Examples 15 or 16 to include a second optical interference filter disposed between the second collimating lens and the second emission detector, wherein the second optical interference filter can be characterized by a second transparent band, and wherein the second optical interference filter can be configured to receive the second collimated emission and in response to pass a portion of the second collimated emission corresponding to the second transparent band toward the second emission detector, and wherein the second optical interference filter can be configured to reflect another portion of the second collimated emission not corresponding to the transparent band toward the first emission detector. Example 16 can include a second focusing lens configured to receive the portion of the second collimated emission passed by the second optical interference filter and in response to pass a second focused emission toward a photo-sensitive region of the second emission detector, wherein the second emission detector can be configured to receive the second focused emission.

Example 18 can include, or optionally can be combined with the subject matter of one or any combination of Examples 15-17 to include the first and second emission detectors, wherein one of the first and second emission detectors can include at least one of a photomultiplier or photodiode configured to detect temporal emission response information from the liquid sample, the other of the first and second emission detectors can include a spectrometer configured to detect spectral emission response information from the liquid sample, and the detected spectral emission response information and the detected temporal emission response information can correspond to the same or a different spectral range.

Example 19 can include, or optionally can be combined with the subject matter of one or any combination of Examples 15-17 to include the first and second emission detectors, wherein the first and second emission detectors can include at least one of a photomultiplier or photodiode, and each of the first and second emission detectors can be configured to detect temporal emission response information from the liquid sample, wherein the temporal emission response information detected by the first and second emission detectors can correspond to the same or different temporal ranges.

Example 20 can include, or optionally can be combined with the subject matter of one or any combination of Examples 15-17 to include the first and second emission detectors, wherein the first and second emission detectors can include a spectrometer configured to detect spectral emission response information from the liquid sample.

Example 21 can include, or optionally can be combined with the subject matter of Example 20 to include the first and second emission detectors, wherein the first and second emission detectors can include a spectrometer configured to detect different bands of spectral emission response information from the liquid sample.

Example 22 can include, or optionally can be combined with the subject matter of one or any combination of Examples 15-21 to include a processor circuit, wherein one of the first and second emission detectors can include a photomultiplier or photodiode configured to detect temporal emission response information from the liquid sample, and wherein the other of the first and second emission detectors can include a spectrometer configured to detect spectral emission response information from the liquid sample. In Example 22, the processor circuit can be configured to use the spectral emission response information from the liquid sample to identify a spectral characteristic of the optical emission from the liquid sample, and wherein the processor circuit can be configured to use the temporal emission response information from the liquid sample to identify a temporal characteristic of the optical emission from the liquid sample.

Example 23 can include, or optionally can be combined with the subject matter of Example 22 to include the processor circuit, wherein the processor circuit can be configured to use the identified spectral characteristic of the optical emission from the liquid sample to determine at least one of a phytoplankton pigment biomass, a phytoplankton community structure, a chromophoric dissolved organic matter content, or an oil content, in the liquid sample.

Example 24 can include, or optionally can be combined with the subject matter of Example 22 to include the processor circuit, wherein the processor circuit can be configured to use the identified temporal characteristic of the optical emission from the liquid sample to determine a magnitude of a chlorophyll-a fluorescence induction.

Example 25 can include, or optionally can be combined with the subject matter of one or any combination of Example 24 to include the processor circuit, wherein the processor circuit can be configured to use the determined magnitude of the chlorophyll-a fluorescence induction to identify at least one of a photo-physiological status or a photochemical efficiency of phytoplankton.

Example 26 can include or use subject matter such as system, such as can include or use a liquid sampling module, an excitation module configured to provide an excitation energy to stimulate a liquid sample, using the liquid sampling module, and a first collimating lens configured to receive an emission from the stimulated liquid sample and in response to pass a collimated emission. In Example 26 the system can include an optical filter configured to receive the collimated emission and in response to pass a spectrally filtered emission, a first emission detector configured to receive the spectrally filtered emission, and a control circuit, coupled to the excitation module and the first emission detector, the control circuit configured to initiate the excitation module to at least one of provide the excitation energy or to initiate the first emission detector to receive the emission, and a processor circuit, coupled to the first emission detector, configured to obtain at least one of a spectral or temporal measurement of the received spectrally filtered emission.

Example 27 can include, or optionally can be combined with the subject matter of one or any combination of Example 26 to include the optical filter, wherein the optical filter includes a band pass spectral filter.

Example 28 can include, or optionally can be combined with the subject matter of one or any combination of Examples 26 or 27 to include the liquid sampling module, wherein the liquid sampling module can include a user-interchangeable liquid measurement cell, configured to contain the liquid sample, wherein the liquid measurement cell can be optically adjacent to a mirror, and wherein the mirror can be configured to reflect, toward the contents of the liquid sampling cell, at least a portion of the excitation energy after the excitation energy has initially stimulated the contents of the liquid sampling cell.

Example 29 can include, or optionally can be combined with the subject matter of one or any combination of Examples 26-28 to include the liquid sampling module, wherein the liquid sampling module can include a second collimating lens and a second mirror, wherein the second collimating lens can be configured to receive a second emission from the stimulated sample and in response to pass a second collimated emission to the second mirror, and wherein the second mirror can be configured to reflect at least a portion of the second collimated emission toward the first emission detector.

Example 30 can include, or optionally can be combined with the subject matter of one or any combination of Examples 26-28 to include a second collimating lens, a second optical filter, and a second emission detector, wherein the second collimating lens can be configured to receive a second emission from the stimulated sample and in response to pass a second collimated emission, the second optical filter can be configured to receive the second collimated emission and in response to pass a first spectral portion of the received second collimated emission toward the second emission detector, and the second optical filter can be configured to reflect a different spectral portion of the received second collimated emission toward the first emission detector.

Example 31 can include, or optionally can be combined with the subject matter of Example 30 to include the second optical filter, wherein the second optical filter can be configured to pass the portion of the received second collimated emission that corresponds to a red spectral band centered at about 685 nm.

Example 32 can include, or optionally can be combined with the subject matter of one or any combination of Examples 30 or 31 to include the first and second emission detectors, wherein one or both of the first and second emission detectors respectively can include a photodiode or a photomultiplier configured to provide respective signals representative of a temporally-resolved emission from the stimulated liquid sample.

Example 33 can include, or optionally can be combined with the subject matter of one or any combination of Examples 30 or 31 to include the first and second emission detectors, wherein one or both of the first and second emission detectors can include a spectrometer configured to provide a signal representative of a spectrally-resolved emission of the stimulated liquid sample.

Example 34 can include, or optionally can be combined with the subject matter of one or any combination of Examples 30 or 31 to include the first and second emission detectors, wherein one of the first and second emission detectors can include a photodiode or photomultiplier, and wherein the other one of the first and second emission detectors can include a spectrometer, wherein information received by the first and second emission detectors can correspond to different spectral ranges of an emission of the stimulated liquid sample.

Example 35 can include, or optionally can be combined with the subject matter of one or any combination of Examples 30 or 31 to include the liquid sampling module, wherein the liquid sampling module can be a user-interchangeable module that includes an optical fiber probe comprising at least two optical fibers.

Example 36 can include, or optionally can be combined with the subject matter of Example 35 to include the liquid sampling module, wherein the liquid sampling module can include a matching lens in an optical path between the optical fiber transmission line and the first emission detector, the matching lens can be configured to receive the emission from the stimulated liquid sample.

Example 37 can include, or optionally can be combined with the subject matter of Example 26 to include the excitation module, wherein the excitation module can include at least one of a laser source, an LED source, or a lamp source, the at least one of the laser source, the LED source, or the lamp source configured to provide the excitation energy as a collimated beam of light.

Example 38 can include, or optionally can be combined with the subject matter of Example 26 to include the processor circuit, wherein the processor circuit can be configured to obtain the spectral measurement using spectral deconvolution (SDC) analysis using information about the received spectrally filtered emissions, and to determine a characteristic of a fluorescent constituent in the liquid sample using information from the SDC analysis.

Example 39 can include, or optionally can be combined with the subject matter of Example 26 to include the liquid sampling module, wherein the liquid sampling module can be a user-interchangeable module that includes one of a flow-through cell, a funnel cell, a reusable static sample cell, or a disposable static sample cell.

Example 40 can include, or optionally can be combined with the subject matter of Example 26 to include the excitation module, wherein the excitation module includes one or more of: a laser configured to provide an electromagnetic excitation energy at or around 514 nm, a laser configured to provide an electromagnetic excitation energy at or around 405 nm, or an ultraviolet excitation source configured to provide an electromagnetic excitation energy at or around 375 nm.

Example 41 can include or use subject matter such as a method, such as can include exciting a liquid at a first time using a first excitation energy, the liquid can include a fluorescent constituent, exciting the liquid at a later second time using a second excitation energy, wherein the second excitation energy can be a reflected portion of the first excitation energy, exciting the liquid at a third time using a third excitation energy, wherein the third excitation energy can be a reflected portion of a first emission from the liquid in response to at least one of the first and second excitation energies, and in response to the exciting the liquid using the first, second, and third excitation energies, receiving, using a processor circuit, information about an emission from the fluorescent constituent of the liquid, the information including at least one of spectral emission intensity response information or temporal emission response information about the emission.

Example 42 can include, or optionally can be combined with the subject matter of Example 41 to include providing, using the processor circuit, an indication of a photo-physiological status of the fluorescent constituent.

Example 43 can include or use subject matter such as a method, such as can include focusing an excitation energy into a first leg of an optical fiber probe to stimulate a liquid sample near an optical output of the probe, receiving, via a second leg of the fiber probe, information from the liquid sample that includes spectral emission intensity response information, using a first emission detector, and receiving, via the second leg of the fiber probe, information from the liquid sample that includes temporal emission response information, using a second emission detector. In Example 44, the method can include determining, using a processor circuit, a characteristic of the liquid sample, including identifying a presence of a fluorescent constituent in the liquid sample, using the received spectral emission intensity response information and the received temporal emission response information.

Example 44 can include, or optionally can be combined with the subject matter of Example 43 to include receiving at least one of the spectral emission intensity response information or the temporal emission response information via a dichroic filter disposed in the light path between the second leg of the fiber probe and the first and second emissions detectors.

The above detailed description includes references to the accompanying drawings, which form a part of the detailed description. The drawings show, by way of illustration, specific embodiments in which the invention can be practiced. These embodiments are also referred to herein as "examples." Such examples can include elements in addition to those shown or described. However, the present inventor also contemplates examples in which only those elements shown or described are provided. Moreover, the present inventor also contemplates examples using any combination or permutation of those elements shown or described (or one or more aspects thereof), either with respect to a particular example (or one or more aspects thereof), or with respect to other examples (or one or more aspects thereof) shown or described herein.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In this document, the terms "including" and "in which" are used as the plain-English equivalents of the respective terms "comprising" and "wherein." Also, in the following claims, the terms "including" and "comprising" are open-ended, that is, a system, device, article, composition, formulation, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

The above description is intended to be illustrative, and not restrictive. For example, the above-described examples (or one or more aspects thereof) may be used in combination with each other. Other embodiments can be used, such as by one of ordinary skill in the art upon reviewing the above description. The Abstract is provided to comply with United States 37 C.F.R. §1.72(b), to allow the reader to quickly ascertain the nature of the technical disclosure. It is submitted with the understanding that it will not be used to interpret or limit the scope or meaning of the claims. Also, in the above Detailed Description, various features may be grouped together to streamline the disclosure. Thus, inventive subject matter may lie in less than all features of a particular disclosed embodiment. The following claims are hereby incorporated into the Detailed Description as examples or embodiments, with each claim standing on its own as a separate embodiment, and it is contemplated that such embodiments can be combined with each other in various combinations or permutations. The scope of the invention should be determined with reference to the appended claims, along with the full scope of equivalents to which such claims are entitled.

The claimed invention is:

1. A system comprising:
a liquid sampling module;
an excitation module configured to provide an excitation energy to stimulate a liquid sample via a first excitation path, using the liquid sampling module;
a first detector path extending from the liquid sampling module to a first emission detector, the first detector path comprising:
a first collimating lens configured to receive an emission from the stimulated liquid sample and in response to pass a first collimated emission;
an optical filter configured to receive tile first collimated emission and in response to pass a spectrally filtered emission and to reflect a reflected emission toward the liquid sample via a second path: and
the first emission detector configured to receive the spectrally filtered emission; and
a second detector path extending from the liquid sampling module to a second emission detector, the second emission detector configured to receive other emissions from the liquid sample when the liquid sample is stimulated by the excitation energy via the first excitation path and is stimulated by the reflected emission via the second path;
a control circuit, coupled to the excitation module and the first and second emission detectors, the control circuit configured to initiate the excitation module to at least one of provide the excitation energy or to initiate the first or second emission detector to receive the emissions; and
a processor circuit, coupled to the first emission detector, configured to obtain at least one of a spectral or temporal measurement of tile received spectrally filtered emission.

2. The system of claim 1, wherein the optical filter includes a band pass spectral filter.

3. The system of claim 1, wherein the liquid sampling module includes a user-interchangeable liquid measurement cell, configured to contain the liquid sample, wherein the liquid measurement cell is optically adjacent to a mirror, and the mirror is configured to reflect, toward contents of liquid sampling cell, at least a portion of the excitation energy provided by the excitation module after the excitation energy provided by the excitation module previously stimulated the contents of the liquid sampling cell.

4. The system of claim 1, wherein the liquid sampling module includes a second collimating lens and a second mirror, wherein the second collimating lens is configured to receive a second emission from the stimulated sample and in response to pass a second collimated emission to the second mirror, and wherein the second mirror is configured to reflect at least a portion of the second collimated emission toward the first emission detector.

5. The system of claim 1, wherein the second detector path further comprises a second collimating lens and a second optical filter;
wherein the second collimating lens is configured to receive a second emission from the stimulated sample and in response to pass a second collimated emission;
wherein the second optical filter is configured to receive the second collimated emission and in response to pass a first spectral portion of the received second collimated emission toward the second emission detector; and
wherein the second optical filter is configured to reflect a different spectral portion of the received second collimated emission toward the first emission detector.

6. The system of claim 5, wherein the second optical filter is configured to pass the portion of the received second collimated emission that corresponds to a red spectral band centered at about 685 nm.

7. The system of claim 5, wherein one or both of the first and second emission detectors respectively comprise a photodiode photomultiplier configured to provide respective signals representative of a temporally-resolved emission from the stimulated liquid sample.

8. The system of claim 5, wherein one or both of the first and second emission detectors respectively comprise a spectrometer configured to provide a signal representative of a spectrally-resolved emission of the stimulated liquid sample.

9. The system of claim 5, wherein one of the first and second emission defectors comprises photodiode or photomultiplier, and therein the other one of the first and second emission detectors comprises a spectrometer, wherein information received by the first and second emission detectors corresponds to different spectral ranges of an emission of the stimulated liquid sample.

10. The system of claim, 1, wherein the liquid sampling module is a user-interchangeable module that includes an optical fiber probe comprising at least two optical fibers.

11. The system of claim 10, wherein the liquid sampling module includes a matching lens in an optical path between the optical fiber transmission line and the first emission detector, the matching lens configured to receive the emission from the stimulated liquid sample and adjust the emission divergence so that it is collimated by the collimating of the first emission detector.

12. The system of claim 1, wherein the excitation module includes at least one of a laser source, an LED source, or a lamp source, the at least one of the laser source, the LED source, or the lamp source configured to provide the excitation energy as a collimated beam of light.

13. The system of claim 1, wherein the processor circuit is configured to obtain the spectral measurement using spectral deconvolution (SDC) analysis using information about the received spectrally filtered emissions, and to determine a characteristic of a fluorescent constituent in the liquid sample using information from the SDC analysis.

14. The system of claim 1, wherein the liquid sampling module is a user-interchangeable module that includes one of a flow-through cell, a funnel cell, a reusable static sample cell, or a disposable static sample cell.

15. The system of claim 1, wherein the excitation module includes one or more of:
   a laser configured to provide an electromagnetic excitation energy at or around 514 nm; and
   a laser configured provide an electromagnetic excitation energy at or around 405 nm.

16. A method comprising:
   focusing an excitation energy into a first leg of an optical fiber probe to stimulate a liquid sample near an optical output of the probe;
   receiving, via a second leg of the fiber probe, information from the liquid sample that includes spectral emission intensity response information, using a first emission detector,
   receiving, via the second leg of the fiber probe, information from the liquid sample that includes temporal emission response information, using a second emission detector; and
   determining, using a processor circuit, a characteristic of the liquid sample, including identifying a presence of a fluorescent constituent in the liquid sample, using the received spectral emission intensity response information and the received temporal emission response information.

17. The method of claim 16, comprising receiving at least one of the spectral emission intensity response information or the temporal emission response information via a dichroic beamsplitter disposed in the light path between the second leg of the fiber probe and the first and second emissions detectors.

18. The method of claim 16, comprising providing, using the processor circuit, an indication of a photo-physiological status of the fluorescent constituent.

19. A system comprising:
   a liquid sampling module;
   an excitation module including an ultraviolet excitation source configured to provide an electromagnetic excitation energy at or around 375 nm to stimulate a liquid sample, using the liquid sampling module;
   a first collimating lens configured to receive an emission from stimulated liquid sample and in response to pass a collimated emission;
   an optical filter configured to receive the collimated emission and in response to pass a spectrally filtered emission corresponding to a specified frequency band to a first emission detector and to reflect a reflected emission toward a second emission detector via an optical path that includes the liquid sample;
   a control circuit, coupled to the excitation module and the first emission detector, the control circuit configured to initiate the excitation module to at least one of provide the excitation energy or to initiate the first emission detector to receive the emission; and
   a processor circuit, coupled to the first emission detector, configured to obtain at least one of a spectral or temporal measurement of the received spectrally filtered emission.

20. The system of claim 19, wherein the processor circuit is configured to obtain the spectral measurement using spectral deconvolution (SDC) analysis using information about the received spectrally filtered emissions, and to determine a characteristic of a fluorescent constituent in the liquid sample using information from the SDC analysis.

* * * * *

UNITED STATES PATENT AND TRADEMARK OFFICE
CERTIFICATE OF CORRECTION

PATENT NO. : 9,618,449 B2  
APPLICATION NO. : 14/376297  
DATED : April 11, 2017  
INVENTOR(S) : Chekalyuk Page 1 of 1

It is certified that error appears in the above-identified patent and that said Letters Patent is hereby corrected as shown below:

In Column 27, Line 66, in Claim 1, delete "tile" and insert --the-- therefor

In Column 28, Line 2, in Claim 1, delete "path:" and insert --path;-- therefor

In Column 28, Line 20, in Claim 1, delete "tile" and insert --the-- therefor

In Column 28, Line 28, in Claim 3, before "the", insert --wherein--

In Column 28, Line 28, in Claim 3, delete "contents of" and insert --the contents of the-- therefor In Column 28, Line 61, in Claim 7, before "photomultiplier", insert --or a--

In Column 29, Line 2, in Claim 9, delete "defectors comprises" and insert --detectors comprises a-- therefor In Column 29, Line 3, in Claim 9, delete "therein" and insert --wherein-- therefor In Column 29, Line 8, in Claim 10, delete "claim," and insert --claim-- therefor In Column 29, Line 17, in Claim 11, before "of", insert --lens--

In Column 29, Line 37, in Claim 15, before "provide", insert --to--

In Column 29, Line 46, in Claim 16, delete "detector," and insert --detector;-- therefor In Column 30, Line 25, in Claim 19, after "from", insert --the--

Signed and Sealed this  
Tenth Day of July, 2018

Andrei Iancu  
*Director of the United States Patent and Trademark Office*